(12) United States Patent
Creusot et al.

(10) Patent No.: US 12,178,963 B2
(45) Date of Patent: Dec. 31, 2024

(54) CONDUIT FOR RESPIRATORY THERAPY APPARATUS

(71) Applicant: ResMed Pty Ltd, Bella Vista (AU)

(72) Inventors: David Creusot, Sydney (AU); Matthew Rolf Harrington, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 311 days.

(21) Appl. No.: 17/705,706

(22) Filed: Mar. 28, 2022

(65) Prior Publication Data

US 2022/0211964 A1 Jul. 7, 2022

Related U.S. Application Data

(63) Continuation of application No. 16/347,855, filed as application No. PCT/AU2017/051219 on Nov. 6, 2017, now Pat. No. 11,318,269.

(Continued)

(51) Int. Cl.
*A61M 16/10* (2006.01)
*A61M 16/00* (2006.01)
(Continued)

(52) U.S. Cl.
CPC ........ *A61M 16/109* (2014.02); *A61M 16/024* (2017.08); *A61M 16/0816* (2013.01);
(Continued)

(58) Field of Classification Search
CPC .............. A61M 16/00; A61M 16/0066; A61M 16/022; A61M 16/024; A61M 16/0816;
(Continued)

(56) References Cited

U.S. PATENT DOCUMENTS

| 4,944,310 A | 7/1990 | Sullivan |
| 7,080,645 B2 | 7/2006 | Genger et al. |
| (Continued) | | |

FOREIGN PATENT DOCUMENTS

| AU | 2009200879 B2 | 5/2014 |
| JP | 2010508875 A | 3/2010 |
| (Continued) | | |

OTHER PUBLICATIONS

Office Action issued in corresponding Japanese Patent Application No. 2023-082921, mailed Nov. 17, 2023, 6 pages.
(Continued)

*Primary Examiner* — Joseph D. Boecker
(74) *Attorney, Agent, or Firm* — Botos Churchill IP Law LLP

(57) ABSTRACT

A respiratory conduit apparatus that conducts a breathable gas for respiratory therapy may include electrical circuit components to assist with therapy. In an example, a delivery conduit for connection with a patient interface and a respiratory therapy device may include a cuff having a microcontroller unit. The cuff may be configured with circuit components for accessory identification, gas characteristic detection for therapy control, heating and communications. In some versions, the delivery conduit may include a controller in a circuit board assembly located at an end of the delivery conduit. The printed circuit board may be configured to control and power the components of the cuff, as well as communicate with a respiratory therapy device.

13 Claims, 16 Drawing Sheets

Related U.S. Application Data

(60) Provisional application No. 62/418,374, filed on Nov. 7, 2016.

(51) Int. Cl.

| | | |
|---|---|---|
| *A61M 16/08* | (2006.01) | |
| *A61M 16/12* | (2006.01) | |
| *A61M 16/16* | (2006.01) | |
| *G06F 1/16* | (2006.01) | |
| *H04W 4/80* | (2018.01) | |
| *H05B 1/02* | (2006.01) | |

(52) U.S. Cl.
CPC .... *A61M 16/0875* (2013.01); *A61M 16/1095* (2014.02); *A61M 16/122* (2014.02); *A61M 16/16* (2013.01); *A61M 16/161* (2014.02); *G06F 1/1683* (2013.01); *H04W 4/80* (2018.02); *H05B 1/025* (2013.01); *A61M 2016/0027* (2013.01); *A61M 2016/0039* (2013.01); *A61M 16/0066* (2013.01); *A61M 2202/0208* (2013.01); *A61M 2205/3368* (2013.01); *A61M 2205/3569* (2013.01); *A61M 2205/3584* (2013.01); *A61M 2205/3592* (2013.01); *A61M 2205/3653* (2013.01); *A61M 2205/50* (2013.01); *A61M 2205/6054* (2013.01); *A61M 2205/8206* (2013.01)

(58) Field of Classification Search
CPC ........... A61M 16/0875; A61M 16/109; A61M 16/1095; A61M 16/16; A61M 2205/3368; A61M 2205/3569; A61M 2205/3653; A61M 2205/50; G06F 1/1683; H05B 1/025
See application file for complete search history.

(56) References Cited

U.S. PATENT DOCUMENTS

| | | |
|---|---|---|
| 7,314,046 B2 | 1/2008 | Schroeder et al. |
| 8,453,641 B2 | 6/2013 | Payton et al. |
| 2001/0017134 A1 | 8/2001 | Bahr |
| 2004/0182392 A1 | 9/2004 | Gerder et al. |
| 2006/0278221 A1 | 12/2006 | Schermeier et al. |
| 2007/0193583 A1 | 8/2007 | Reed |
| 2008/0105257 A1 | 5/2008 | Paul et al. |
| 2008/0200776 A1 | 8/2008 | Kullik et al. |
| 2009/0223514 A1 | 9/2009 | Smith et al. |
| 2010/0151785 A1 | 6/2010 | Steeger et al. |
| 2011/0011400 A1 | 1/2011 | Gentner et al. |
| 2011/0023874 A1* | 2/2011 | Bath ................ A61M 16/0069 128/203.14 |
| 2011/0088693 A1* | 4/2011 | Somervell ............ A61M 16/16 128/203.14 |
| 2011/0162647 A1* | 7/2011 | Huby .................... A61M 16/16 128/203.14 |
| 2011/0232645 A1 | 9/2011 | Smith |
| 2012/0125333 A1* | 5/2012 | Bedford ............. A61M 16/109 128/205.12 |
| 2012/0229272 A1 | 9/2012 | Jacob et al. |
| 2014/0069428 A1 | 3/2014 | Sears et al. |
| 2014/0216459 A1* | 8/2014 | Vos ..................... A61M 16/16 128/204.17 |
| 2014/0283831 A1 | 9/2014 | Foote et al. |
| 2014/0305431 A1 | 10/2014 | Holley et al. |
| 2015/0027204 A1* | 1/2015 | Stoks .................... G01K 13/02 73/31.05 |
| 2015/0101600 A1* | 4/2015 | Miller ................. A61M 16/161 128/203.14 |
| 2015/0165142 A1 | 6/2015 | Tham et al. |
| 2015/0297306 A1 | 10/2015 | Lazar et al. |
| 2016/0008560 A1 | 1/2016 | Kwok |
| 2016/0256657 A1 | 9/2016 | Klasek et al. |
| 2016/0354573 A1* | 12/2016 | Buswell ........... A61M 16/0875 |
| 2018/0280651 A1* | 10/2018 | Liu .................... A61M 16/161 |
| 2020/0001037 A1* | 1/2020 | Liu ..................... A61M 16/024 |

FOREIGN PATENT DOCUMENTS

| | | |
|---|---|---|
| JP | 2015536754 A | 12/2015 |
| JP | 2016516537 A | 6/2016 |
| WO | 2007051230 A1 | 5/2007 |
| WO | 2008055308 A1 | 5/2008 |
| WO | 2010027282 A2 | 3/2010 |
| WO | 2014077706 A1 | 5/2014 |
| WO | 2014088430 A1 | 6/2014 |
| WO | 2014165116 A1 | 10/2014 |
| WO | 2014176454 A1 | 10/2014 |

OTHER PUBLICATIONS

Extended European Search Report for Application No. EP21217868 dated May 10, 2022.
Japanese Notice of Reasons for Rejection for Application No. P2019-544942 dated Jul. 8, 2022.
International Search Report for PCT/AU2017/051219 mailed Mar. 13, 2018.
Notice of Reasons for Refusal for Japanese Patent Application No. 2019-544942, Oct. 5, 2021.
The Extended European Search Report for European Patent Application No. 17866537.8, Jun. 9, 2020.
Extended European Search Report issued in corresponding European Patent Application No. 24151999.0, mailed Jul. 16, 2024, 8 pages.

* cited by examiner

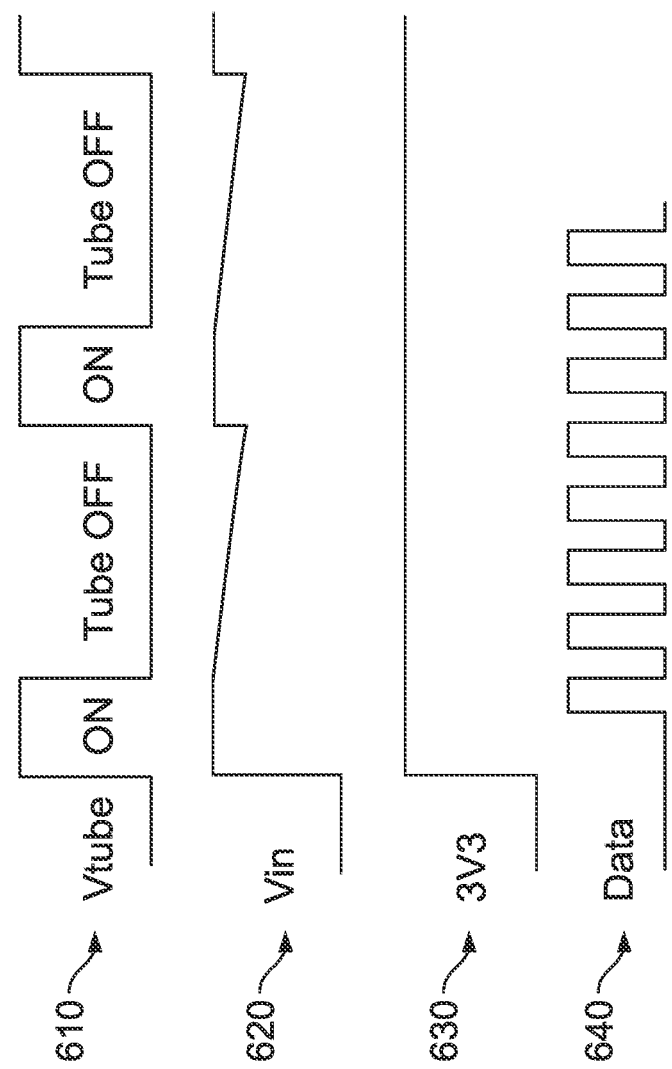

CONDUIT FOR RESPIRATORY THERAPY APPARATUS

CROSS REFERENCE

This application is a continuation of U.S. application Ser. No. 16/347,855, filed on May 7, 2019, which is a national phase entry under 35 U.S.C. § 371 of International Application No. PCT/AU2017/051219 filed Nov. 6, 2017, published in English, which claims priority from U.S. Provisional Patent Application No. 62/418,374 filed Nov. 7, 2016, all of which are incorporated herein by reference.

FIELD OF THE TECHNOLOGY

The present technology relates to apparatus for breathable gas therapy for respiratory conditions such as the conditions related to obstructive sleep apnea (OSA), sleep disordered breathing (SDB), allergy induced upper airway obstruction or early viral infection of the upper airway, among others. More particularly, the technology involves improvements related to delivery conduit components for such respiratory treatment apparatus.

BACKGROUND OF THE TECHNOLOGY

Sleep is important for good health. Frequent disturbances during sleep or sleep fragmentation can have severe consequences including day-time sleepiness (with the attendant possibility of motor-vehicle accidents), poor mentation, memory problems, depression and hypertension. For example, a person with nasal congestion may snore to a point that it disturbs that person's ability to sleep. Similarly, people with Obstructive Sleep Apnea (OSA) are also likely to disturb their partner's sleep. The best form of treatment for patients with OSA is Continuous Positive Airway Pressure (CPAP) applied by a flow generator such as a blower (or compressor) via a connecting delivery hose with a patient interface.

CPAP therapy has been used to treat OSA. The continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist patient breathing and/or maintain adequate oxygen levels in the body by doing some or all of the work of breathing. The ventilatory support is provided via a non-invasive patient interface. NIV has been used to treat OSA, respiratory failure, and periodic breathing. In some forms, the comfort and effectiveness of these therapies may be improved.

Such positive airway pressure may be delivered in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly replicate changes in the patient's breathing cycle. A pressure setting during expiration lower than inspiration may generally be referred to as expiratory pressure relief. As described by Sullivan in U.S. Pat. No. 4,944,310, positive airway pressure treatments typically provide gas under pressures to the patient in the range of 4 to 15 $cmH_2O$ from the device and may involve flow rates of up to about 120 liters/minute. Some of the air may escape via an end restriction or vent and not be delivered to the patient. These pressure settings may also be adjusted based on the detection of conditions of the patient's airway. For example, treatment pressure may be increased in response to the detection of partial obstruction, apnea, hypopnea or snoring, etc.

Other devices are known for providing respiratory tract therapy. For example, Schroeder et al. describes an apparatus for delivering heated and humidified air to the respiratory tract of a human patient in U.S. Pat. No. 7,314,046. Similarly, Genger et al. discloses an anti-snoring device with a compressor and a nasal air cannula in U.S. Pat. No. 7,080,645.

A typical system of the present technology may include a respiratory therapy device, such as a Respiratory Pressure Therapy Device (RPT device), an air circuit, a humidifier, and a patient interface.

Patient Interface

A patient interface may be used to interface respiratory equipment to its user, for example by providing a flow of air to an entrance to the airways. The flow of air may be provided via a mask to the nose and/or mouth, a tube to the mouth or a tracheostomy tube to the trachea of the user. Depending upon the therapy to be applied, the patient interface may form a seal, e.g., with a face region of the patient, to facilitate the delivery of gas at a pressure at sufficient variance with ambient pressure to effect therapy, e.g., a positive pressure of about 10 $cmH_2O$. For other forms of therapy, such as the delivery of oxygen, the patient interface may not include a seal sufficient to facilitate delivery to the airways of a supply of gas at a positive pressure of about 10 $cmH_2O$.

Different types of patient interfaces may be known by a variety of names by their manufacturer including nasal cannulas, nasal masks, full-face masks, nasal pillows, nasal puffs and oro-nasal masks.

Air Circuit

An air circuit, such as one or more conduits, may pneumatically couple between a flow generator and a patient interface, to transfer breathable gas (e.g., air and/or oxygen) between the devices. The air circuit may be referred to as an air delivery tube or a delivery conduit. In some cases there may be separate limbs of the circuit for inhalation and exhalation. In other cases a single limb is used.

Respiratory Pressure Therapy (RPT) Device

One known RPT device used for treating sleep disordered breathing is the S9 Sleep Therapy System, manufactured by ResMed. Another example of an RPT device is a non-invasive ventilator.

RPT devices typically comprise a pressure or flow generator, such as a motor-driven blower (e.g., a servo controlled motor and impeller in a volute) or a compressed gas reservoir, and are configured to supply a flow of air to the airway of a patient. In some cases, the flow of air may be supplied to the airway of the patient at positive pressure. The outlet of the RPT device is connected via the air circuit the patient interface such as those described above. An RPT device may be referred to as a respiratory therapy device herewithin.

Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfill the specialised requirements of a medical humidifier.

Respiratory humidifiers are available in many forms and may be a standalone device that is coupled to an RPT device via an air circuit, integrated with the RPT device or configured to be directly coupled to the relevant RPT device.

There is a desire for improved exchange of information between components of a respiratory therapy system with each other, and with the user. Operation of the respiratory therapy system as a whole may be improved as a result, as may the resulting therapy provided to the user, such as in terms of comfort, quality of therapy and/or compliance.

Furthermore, it may be desirable to introduce additional functionalities to components, for example to interact with other components of a respiratory therapy system, with the user, or in a standalone capacity. Prior solutions for communication within components of respiratory therapy systems may be inconvenient, difficult to use or expensive. In some cases, prior solutions for components of respiratory therapy systems may be of limited functionality, or may not be configured to take advantage of the particular configurations of the rest of the respiratory therapy system.

It may be desirable to further develop these devices, such as the air circuit or air tube delivery, for improvements in operations between and the interrelated components of such respiratory therapy systems.

SUMMARY OF THE TECHNOLOGY

In an aspect of the present technology, systems, apparatus and methods provide respiratory treatment for a patient.

Some versions of the present technology may include a breathable gas delivery conduit such as for a respiratory therapy device, such as for coupling with the device and/or a patient interface.

Some versions of the present technology may include such a delivery conduit with a control circuit, such as one including a wireless transceiver.

Some versions of the present technology may include such a delivery conduit with an integrated controller having one or more sensors to detect a condition of a breathable gas of the delivery conduit.

Some versions of the present technology may include such a delivery conduit with an integrated controller able to detect attachment of an accessory or patient interface to the delivery conduit.

Some versions of the present technology may include such a delivery conduit with an integrated controller configured to wirelessly receive identification information from an accessory or patient interface attached to the delivery conduit.

Some versions of the present technology may include a respiratory apparatus for coupling with a respiratory therapy device that generates a flow of breathable gas and a patient interface that delivers the flow of breathable gas to a patient. The respiratory apparatus may include a delivery conduit having a gas passage configured to conduct the generated flow of breathable gas from the respiratory therapy device to the patient interface. The delivery conduit may have a respiratory therapy device coupler end and a patient interface coupler end. The delivery conduit may have a length extending from the respiratory therapy device coupler end to the patient interface coupler end. The respiratory apparatus may include a wireless transceiver mounted on the delivery conduit at a point along the length of the delivery conduit closer to the patient interface coupler end than to the respiratory therapy device coupler end.

In some versions, the wireless transceiver may be configured to detect a transmitted accessory identifier from an accessory coupled at the patient interface coupler end. The wireless transceiver may be configured to read one of a radio frequency identification tag and a near field communication identification tag from an accessory coupled at the patient interface coupler end. The accessory may be a patient interface for delivering the flow of breathable gas from the delivery conduit to the patient. The wireless transceiver may be coupled to a controller, and may be configured to relay data comprising an identification of an accessory to the controller. The controller may be located at the respiratory therapy device. The controller may be located on circuit board on the delivery conduit, and wherein the wireless transceiver may be configured to relay the data comprising an identification of an accessory to the controller over a wired connection. The controller may be configured to relay the data comprising an identification of an accessory to a controller of the respiratory therapy device. The respiratory apparatus may include two or more wires extending along the length of the delivery conduit. The respiratory apparatus may include a first inductive connector adapted for connection to a power supply via the two or more wires of the delivery conduit. The respiratory apparatus may include a second inductive connector connected to circuit components of a controller to conduct power to the circuit components of the controller, the circuit components of the controller configured in a cuff adapted to couple to an end of the delivery conduit. The first inductive connector may be configured to inductively transfer power to the second inductive connector.

In some versions, at least one controller may be configured to determine a duration of use of an accessory attached to the patient interface coupler end. The apparatus may include the respiratory therapy device. A controller in the respiratory therapy device may be configured to operate a first switch to power a controller in the patient interface coupler end and the controller in the patient interface coupler end is configured to operate a second switch to intermittently control heating of the breathable gas flowing through the delivery conduit and data communication between the controllers. The respiratory therapy device may include a humidifier and a flow generator.

Some versions of the present technology may include a respiratory apparatus control device. The device may include a breathable gas delivery conduit for a respiratory therapy device. The breathable gas delivery conduit may be adapted to connect to an outlet of an airflow generator of the respiratory therapy device and may be adapted to connect to a breathable gas inlet of a patient interface. The device may include a flexible printed circuit board having a surface bent around a portion of the breathable gas delivery conduit. The device may include controller mounted to the surface of the flexible printed circuit board. The controller may be configured to control a determination of one or more parameters for the respiratory therapy device.

In some versions, the flexible printed circuit board may include a communications interface. The communications interface may be adapted to connect to one or more wires of a data bus along the delivery conduit. The controller may be configured to control the communications interface to transmit data signals on the data bus. The device may include a wireless transceiver mounted to the surface of the flexible printed circuit board. The wireless transceiver may be configured to communicate with one or both of: a transceiver of a controller of a respiratory therapy device; and an identification circuit of a patient interface. A parameter of the one or more parameters may be a characteristic of a breathable gas delivered through the delivery conduit from the respiratory therapy device. A parameter of the one or more parameters may be a characteristic of a patient interface coupled to an end of the delivery conduit. The controller mounted to the surface of the flexible printed circuit board may be configured to communicate a measurement of a characteristic of a breathable gas in the delivery conduit to a controller of the respiratory therapy device for close loop control of the characteristic of the breathable gas. The controller mounted to the surface of the flexible printed circuit board may be configured to determine a measurement of a characteristic of a breathable gas in the delivery conduit and to control the characteristic of the breathable gas. The controlled characteristic of the breathable gas may be temperature and the controller may be configured to operate a heater element of the delivery conduit.

In some versions, the controller mounted to the surface of the flexible printed circuit board may be configured to detect connection and disconnection of a patient interface to the delivery conduit and may be configure to generate a data signal to a controller of a respiratory therapy device for controlling operation of the respiratory therapy device based on the detection. The flexible printed circuit board may include one or more sensors mounted to the surface. The surface of the flexible printed circuit board may include an extension strip bent to extend through an aperture of the portion of the delivery conduit into a gas passage of the delivery conduit to extend a sensor mounted to the extension strip into the gas passage for sensing a characteristic of the gas of the gas passage of the delivery conduit. The one or more sensors may be adapted to measure at least one or more of pressure, air flow, temperature, and relative humidity of air delivered through the delivery conduit. The portion of the delivery conduit may include a cylindrical cuff of the delivery conduit adapted for removable coupling with a patient interface. The cylindrical cuff may further include a sheath to enclose the flexible printed circuit board. The cylindrical cuff may include a gas passage of the delivery conduit and the gas passage may include a heater element controlled by the controller mounted to the surface of the flexible printed circuit board. The controller mounted to the surface of the flexible printed circuit board may be configured to communicate data and to heat the delivery conduit through a set of wires by intermittently switching between heating operations and data signaling operations. The set of wires may extend along the delivery conduit and may consist of three wire conductors.

Some versions of the present technology may include a respiratory apparatus. The respiratory apparatus may include a respiratory therapy device to generate a flow of breathable gas. The respiratory apparatus may include a delivery conduit to conduct the generated flow of breathable gas from the respiratory therapy device to a patient interface. The respiratory apparatus may include a first controller located at the respiratory therapy device. The respiratory apparatus may include a second controller located at or adjacent to a patient-end of the delivery conduit. The respiratory apparatus may include a set of wires along the delivery conduit connecting the first controller and the second controller. The set of wires may include three wires for both heating of the delivery conduit and for data communication between the first controller and the second controller. One or both of the first controller and second controller may be configured to interleave communication operations and heating operations in alternating fashion through the set of wires.

In some versions, the set of wires may include a first wire, a second wire, and a ground wire. The first wire and ground wire may provide for data communication between the first controller and the second controller. The second wire and said ground wire may provide heat for the delivery conduit using power from a power supply of the respiratory therapy device. The respiratory apparatus may include a first switch located at the respiratory therapy device that may be controlled by the first controller, and a second switch located at the delivery conduit that may be controlled by the second controller. Closing each of the first switch and the second switch may control a heating operation. Closing the first switch and opening the second switch may permit control of a communication operation. The communication operation may include a transmission of a measurement from one or more sensors in the delivery conduit. In some cases, the one or more sensors may be configured to measure at least one of air flow, pressure, temperature, and relative humidity in the delivery conduit. The communication operation may include a transmission of an identification of an accessory coupled to the delivery conduit.

In some versions, the respiratory apparatus may include a cuff and sheath attached to the patient end of the delivery conduit. The second controller may be disposed on the cuff and covered by the sheath.

Some versions of the present technology may include a control method for a respiratory apparatus. The respiratory apparatus may include a respiratory therapy device to generate a flow of breathable gas, a delivery conduit to conduct the generated flow of breathable gas from the respiratory therapy device to a patient interface, and a set of wires to couple a first controller with a second controller, the set of wires extending along the delivery conduit and separating the first controller and the second controller. The control method may include receiving data through the set of wires at the first controller in a communications operation. The control method may include transmitting the data through the set of wires from the second controller in said communications operation. The control method may include heating the set of wires with one or both of the first controller and second controller in a heating operation to heat a flow of breathable gas through the delivery conduit. The control method may include interleaving the heating operation and the communications operation.

In some versions, the data of the communications operation indicates one or more of flow, pressure, temperature, and relative humidity of the breathable gas flowing through the delivery conduit. The heating operation may be controlled by a pulse width modulation signal.

Some versions of the present technology may include a method for constructing a delivery conduit assembly. The delivery conduit assembly may be for conducting a flow of breathable gas from a respiratory therapy device to a patient interface. The delivery conduit may have a cuff connector end. The method may include wrapping and affixing a flexible printed circuit board about an outer surface of the cuff connector end so as to bend a surface of the flexible printed circuit board into a cylindrical form. The cuff connector end may include a cylindrical gas passage and may have open first and second ends. The method may include attaching an end of the tube to the cuff connector end. The method may include covering the printed circuit board and at least a portion of the cuff connector end with a sheath.

In some versions, the method may include inserting an extension strip of the flexible printed circuit board into an aperture through the cuff connector end to insert a sensor mounted on the extension strip into the cylindrical gas passage of the cuff connector end. The method may include capping the sensor and an end of the extension strip with a cap before the inserting. The method may include affixing to terminals on the flexible printed circuit board one or more wires of a set of wires of tube. The method may include coiling a wire antenna about a channel of the cuff connector end and affixing wire ends of the wire antenna to terminals of the printed circuit board. The method may include removably coupling the cuff connector end to a patient interface. The method may include removably attaching an end of the tube to a respiratory therapy device generator using a coupler.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF DRAWINGS

The present technology is illustrated by way of example, and not by way of limitation, in the figures of the accompanying drawings, in which like reference numerals refer to similar elements including:

FIG. 6 illustrates an example control scheme for the system shown in FIG. 5.

DETAILED DESCRIPTION

Figure 1:
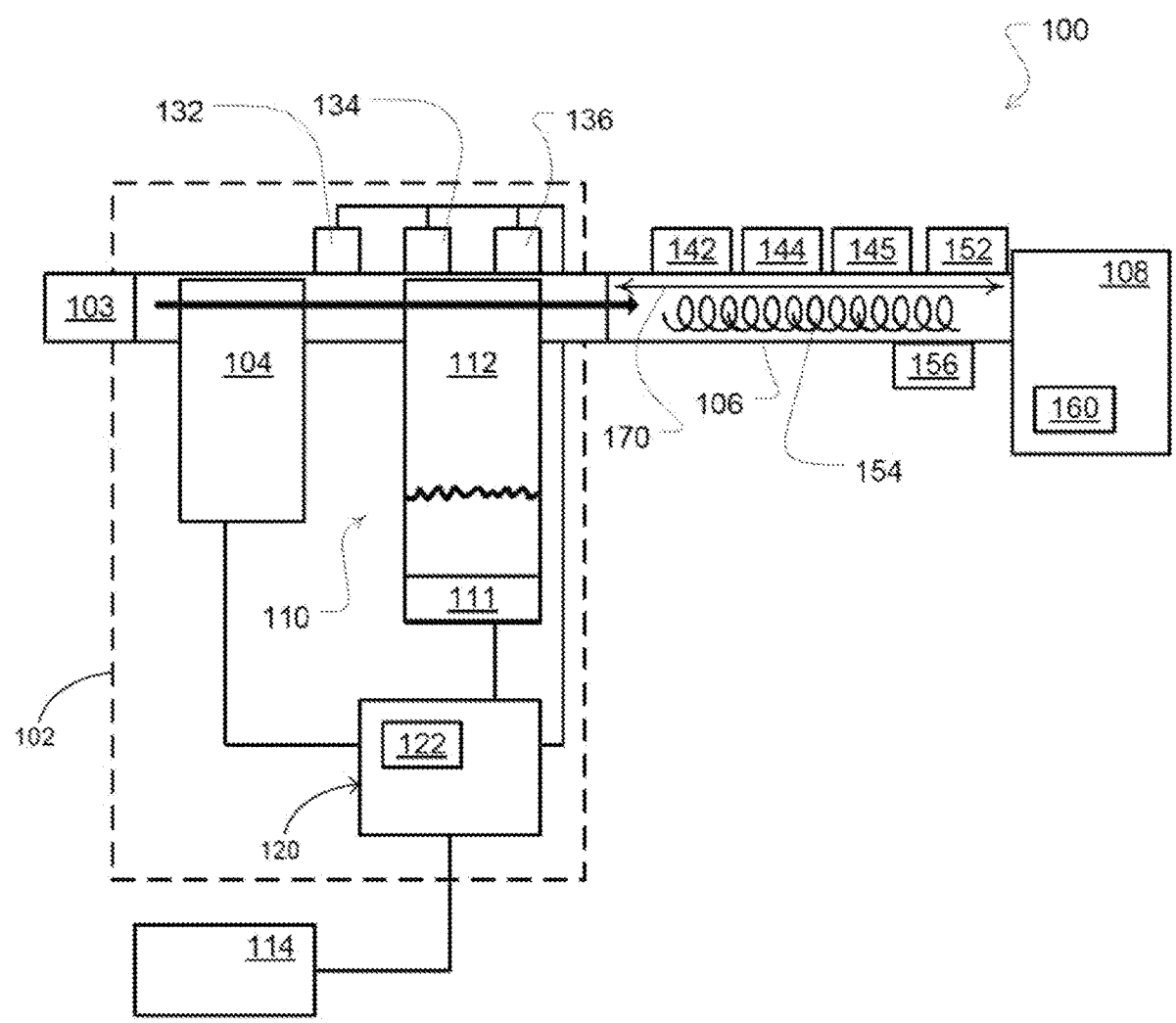
FIG. 1 is a block diagram of an example respiratory therapy system for respiratory treatment of the airway of a patient.

Examples of the present technology may be considered in relation to the respiratory therapy system 100, including some or all of the components illustrated in FIG. 1. An implementation of such components may also be considered in reference to the illustration of FIG. 2. For example, the respiratory therapy system 100 may include a respiratory therapy device 102 that will typically include a flow generator such as a servo-controlled blower 104. The blower 104 will typically include an air inlet and impeller driven by a motor (not shown). Optionally, oxygen may be introduced upstream or downstream of the blower to mix with or supplement the breathable gas supplied by the impeller to the airway of a user. Moreover, an air filter 103 may be provided, such as a HEPA filter, to remove dust or other allergens from the air drawn into the air inlet. The blower may optionally be configured for generating varied flows or varied pressures associated with a patient respiratory cycle depending on the type of treatment (e.g., CPAP, bi-level, APAP etc. such as a pressure in an example range of 4 to 40 $cmH_2O$, such as 4 to 15 $cmH_2O$ or 4 to 25 $cmH_2O$) and it may further be adjusted based on respiratory conditions (e.g., apnea, hypopnea, obstruction, etc.) detected by the apparatus (e.g., apnea, hypopnea, obstruction, etc.).

The respiratory therapy device 102 may be configured to be connected to a breathable gas delivery conduit 106 and a patient interface 108 to deliver the flow of air or breathable gas to the upper airway(s) of a user of the device or patient. In one example, the patient interface may be a nasal mask or mouth and nose mask (example shown in FIG. 2) coupled with the delivery conduit. The delivery conduit 106 may include a pneumatic coupler at each end to couple respectively with corresponding couplers of the patient interface 108 and respiratory therapy device 102 such as at an output of the blower or a volute of the blower or output of a humidifier.

According to one aspect, the humidifier 110 is configured to add humidity to a flow of air from the RPT device 102 as the flow of air travels therethrough. In one form, the humidifier 110 may be configured to encourage the flow of air to travel in a tortuous path through the reservoir 112 while in contact with the volume of water therein.

Figure 2:
FIG. 2 is a perspective view of a form of the respiratory treatment system shown in FIG. 1 in use by a patient.

Thus, the respiratory therapy device 102 may include a humidifier 110, which may comprise a humidifier reservoir 112 and a humidifier heater 111. The humidifier may be configured or controlled to heat and/or humidify the breathable gas to a desired temperature and/or humidity. For example, the humidifier may be configured that the breathable gas may pass through or proximate with or to a fluid or vapor of the humidifier reservoir 112. The heater 111 may include one or more heating elements and/or heating plates to heat the fluid contained in the humidifier reservoir 112. In one embodiment, the heater may be based on a film laminate heater that may be fitted by adhesive to the base of a heater plate. The heater element may include a temperature sensor on the heater film. As a further option, while the heater 111 is in contact with the liquid of the reservoir of the humidifier, an additional heater that is not in contact with the liquid of the reservoir may also heat the breathable gas from the flow generator that passes through the humidifier. The humidifier may be removably coupled with the respiratory therapy device 102 as shown in FIG. 2, or may be integrally constructed with the respiratory therapy device 102.

The respiratory treatment device may also include a controller 120 for controlling any or all of the above-described components, including the blower 104 and heater 111. For instance, the controller, which may include one or more processors such as a programmable processor or an application specific integrated chip, may control the amount of power supplied by a power supply 114 to the controlled components. The power supply 114 may include a battery, either integrated into the respiratory therapy device 102 or housed in a separate module electrically coupled to the respiratory therapy device 102. The power supply 114 may additionally or alternatively include or couple with an AC/DC transformer such as for receiving power from a mains power supply. In some cases, the conduit may include its own power supply such as by including a battery in the delivery conduit 106 (e.g., in its cuff).

The respiratory therapy system 100 may comprise one or more sensors. The controller 120 may be coupled to, or receive signals from, the one or more sensors, such as a flow (also referred to as a flow rate) sensor, temperature sensor, pressure sensor, relative humidity sensor, etc., to receive sensor data, and to determine control operations of the respiratory therapy device 102 based on the received sensor data. In some examples, one or more sensors may be configured to sense conditions in relation to one or more of the blower 104 and the humidifier 110 so as to provide data and/or signals concerning such conditions. For example, a flow sensor 132 may be positioned at or near an inlet of the blower, within the blower, outlet of the blower 104 or volute of the blower, and temperature and humidity sensors 134, 136 may be positioned at or near the humidifier reservoir 112. The temperature and humidity sensors generate temperature or humidity signals for controlling or setting temperature and/or humidity of the device.

Some sensors may be located for measuring ambient conditions. Alternatively or additionally, one or more sensors, such as sensors 142, 144, 145 may be positioned downstream in the delivery conduit 106, for instance, at or near the patient interface 108. Such sensors of the delivery conduit may be, for example, one or more of pressure, humidity, temperature, and flow sensors. For example, such sensors may be pressure, humidity and temperature sensors.

Additional components for the respiratory therapy system 100 may also be included at or integrated within the delivery conduit 106 to complement and/or function with the components of the respiratory therapy device 102 or other parts of the system. These additional components may improve the communication of information among the respiratory therapy device 102, such as with its controller, the humidifier 110, the delivery conduit 106, and the patient interface 108. The additional devices may also provide additional (or improved) functionality to the respiratory therapy system 100. For example, different sets of components (e.g., sensors) may be included in different versions of the delivery conduit. These sets of components of the delivery conduit may then be utilized by the controller of the respiratory therapy device 102 when the different/new delivery conduit version is connected to the respiratory therapy device 102. For example, the controller may detect coupling of a new delivery conduit and change operations, such as treatment operations, depending on the capabilities of the accessory components of the newly coupled delivery conduit. In this regard, the delivery conduit may be configured with components to permit electronic communications (e.g., wired or wireless) between the delivery conduit and the respiratory therapy device 102 (e.g., controller 120). Utilization of delivery conduits having control circuits and sensors can permit ready replacement and upgrading of components for the maintaining or upgrading operation of respiratory therapy device to which they may be used.

For example, a wireless transceiver 152, such as a radio frequency identification (RFID) reader or near field communication (NFC) reader, may be provided in or on the delivery conduit to assist in relaying information between components of the respiratory therapy device 102. The transceiver may, for example, be provided close to a patient-end or proximal the end of the delivery conduit (e.g., closer to the end of the delivery conduit connected to the patient interface 108 than to the end connected to the blower 104), and configured to read data stored on a transmitter 160 or other identification circuit, such as an RFID tag or NFC tag, of a device coupled to the delivery conduit. For example, when a patient interface 108 with such a transmitter or tag is activated, or coupled to the delivery conduit, it may transmit its data to the transceiver of the delivery conduit. Such transmittable data may indicate one or more of the type, model number, production date, or any other relevant information about the connected device or patient interface 108, information in relation to use of the connected device, and information in relation to the user. In some cases, the wireless transceiver may be, alternatively or additionally, implemented for such transmissions using other wireless protocols, such as, for example, Bluetooth or Bluetooth LE.

The wireless transceiver 152 may also communicate information to a control processor, such as controller 120 of the respiratory therapy device 102, or to a secondary controller 156 (e.g., microprocessor or microcontroller) located towards or at a proximal (patient end) of the respiratory therapy system, for example integrated with the delivery conduit 106 (discussed in more detail below). The information communicated by the transceiver may include, for example, sensor data (e.g., from sensors 142, 144 or 145), sensor configuration/type, and/or tag data (e.g., from tag or transmitter 160). In some cases, the secondary controller 156 may relay data obtained from the transceiver by sending the data to the controller 120 of the respiratory therapy device 102. The controller 120 may then utilize the relayed information to customize control operations, such as to meet specific preferences or requirements of the patient interface 108 or therapy control. Alternatively or additionally, the controller 120 may use the relayed information to determine how long the patient interface has been in use (e.g., based on a first time the patient interface was detected by the transceiver, based on a total duration of time for which the patient interface has been detected by the transceiver), and may control operations, such as generating time of use related warnings, accordingly. The transceiver may similarly be capable of reading and relaying data stored on other accessories connected to the respiratory therapy device in order to further customize operation of the device.

In some versions, the delivery conduit control circuit may include a sensor configured to determine a presence (or absence) of an attachable accessory/component. For example, an inductive proximity sensor may be located in a cuff. In some such versions, the sensor may determine a presence of the accessory (e.g., a patient interface) such as with a metal (ferromagnetic) ring.

Information from the delivery conduit sensors (e.g., sensors 142, 144, 145) and/or transceiver 152 may be relayed to the controller 120 by either wired or wireless signaling or communication. For example, wired communications may be implemented via a wired data bus 170 of a set of wires extending along the delivery conduit including two or more wires extending the length of the delivery conduit from the respiratory therapy device 102 to the transceiver. Wireless communications may be implemented with the transceiver 152 and an optional second transceiver 122 integrated with or coupled to the controller 120 within the respiratory therapy device 102. Wireless communications from the transceiver 152 may be implemented via a direct wireless connection between the respiratory therapy device transceiver and the conduit transceiver, or via any number of intermediate communications links, such as via a remote control, a smartphone, an internet such the Internet, etc. Such communications can provide the controller 120 with information to, for example, adjust parameters and settings of a therapy provided with the controller 120. For example, such information from sensors can serve as input to any control loop implemented by the controller 120 with the respiratory therapy device (e.g., pressure control, temperature control, flow control, humidity control, etc.).

In some cases, the delivery conduit may also include one or more heater or heating element(s), such as a delivery tube heater 154. These components may be provided in or on the delivery conduit 106, such as substantially along its gas path, to assist with maintaining the temperature of the breathable gas after it passes from the humidifier or flow generator into the delivery conduit. In some versions, one or more heater or heating element(s) may be isolated at an end portion, such as within a cuff, of the delivery conduit. Thus, the delivery conduit may have one or more heating elements along the gas path and/or within a cuff of the delivery conduit. By keeping the delivery conduit warm, condensation in the delivery tube may be reduced or avoided as the breathable gas traverses the delivery tube toward the patient. The secondary controller 156 may be operatively coupled to the sensors in the delivery conduit, and may be responsible for processing information received from the sensors. The secondary controller 156 may further be operatively coupled to accessory devices in the delivery conduit, such as its heating elements or the delivery tube heater 154, in order to regulate the temperature of the breathable gas in the delivery conduit.

In some versions, the secondary controller 156 may receive a measurement signal from a humidity sensor 145 indicating an amount of moisture buildup in the delivery conduit. Based on the received measurement, the secondary controller 156 may communicate the received information to the controller 120 located at the blower so as to provide information for controlling heating of the breathable gas flowing through the delivery conduit. Similar functions may be performed for other parameters of the breathable air passing through the delivery conduit, such as temperature, pressure and/or flow from other sensors of the delivery conduit. In some versions, the secondary controller 156 may receive the sensed measurement(s), and may itself control heating of the breathable gas in response to the measurement such as by selectively activating/operating the heating elements of the delivery conduit. In some such versions, any of the controllers may be operatively coupled to a switch to control opening (i.e., breaking) or closing (i.e., completing) a heating circuit for the heating elements of the delivery conduit.

The secondary controller 156 of the delivery conduit may also receive information (e.g., from the wireless transceiver) indicating whether a patient interface is or is not connected to the delivery conduit so as to detect the connection of the patient interface. Such information may serve as a control signal such as for permitting or prohibiting activation of one or more components of the delivery conduit and/or respiratory therapy device 102. For example, if no patient interface is detected, the secondary controller 156 may communicate an indication of the absence of a patient interface to the controller 120 of the respiratory therapy device 102. Either controller may control the heating elements, such as via the aforementioned switch, to prevent heating, such as of the delivery conduit, while the patient interface is disconnected such as in the sense of an override. Similarly, information concerning detection of the connected patient interface may serve as a control signal, which may be communicated to the controller 120, to permit activation of the heating element(s), such as the elements of the delivery conduit.

In some versions, the heater 154 may be implemented with a first subset of wires, such as two or more wires, of a set of wires extending along or embedded in the delivery conduit. The wires may be heating elements designed to warm and transfer heat to the passing breathable gas by an application of electrical current to the wires. The heater 154 may be included in one or more of: the tubing of the delivery conduit, or a cuff attached to an end of the delivery conduit at which the conduit connects to the patient interface. The cuff may serve as a coupler for removeably connecting the delivery conduit to a corresponding coupler of the patient interface for use.

Figure 3:
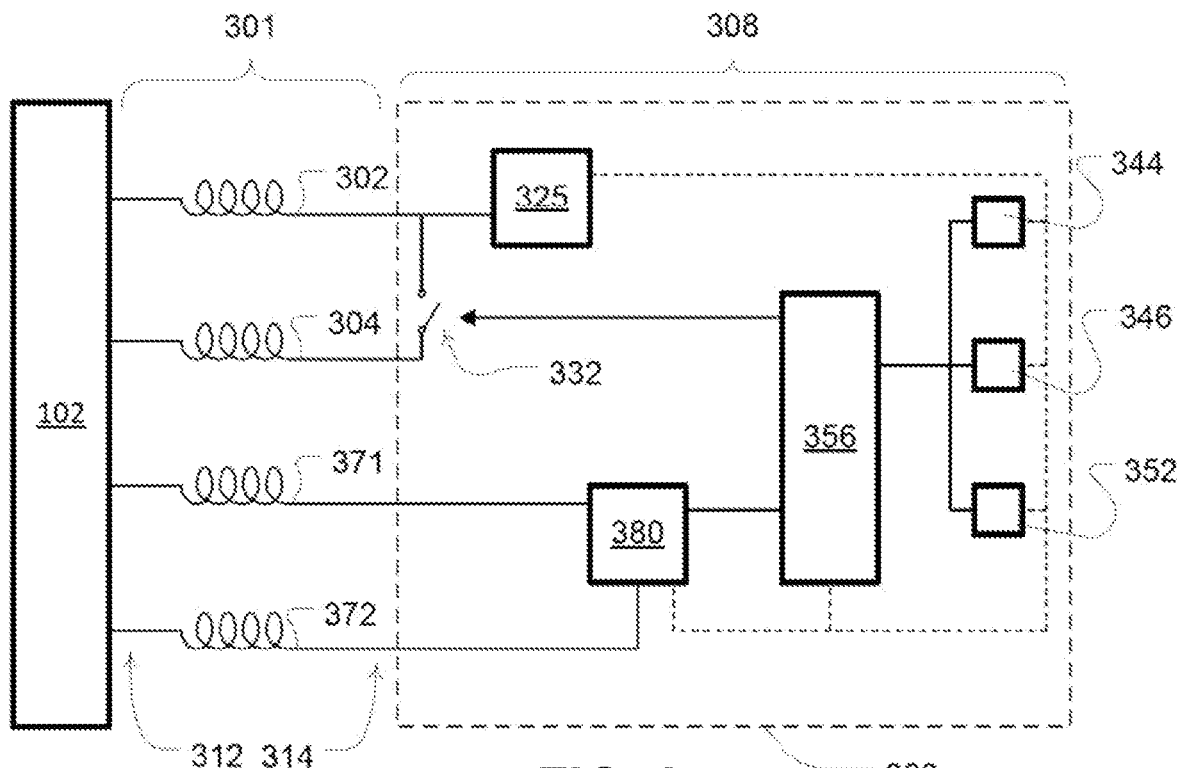
FIG. 3 is a block diagram illustrating a respiratory therapy system including heating and signaling components in a delivery conduit having a heated tube, in accordance with an example of the present technology.
Figure 4:
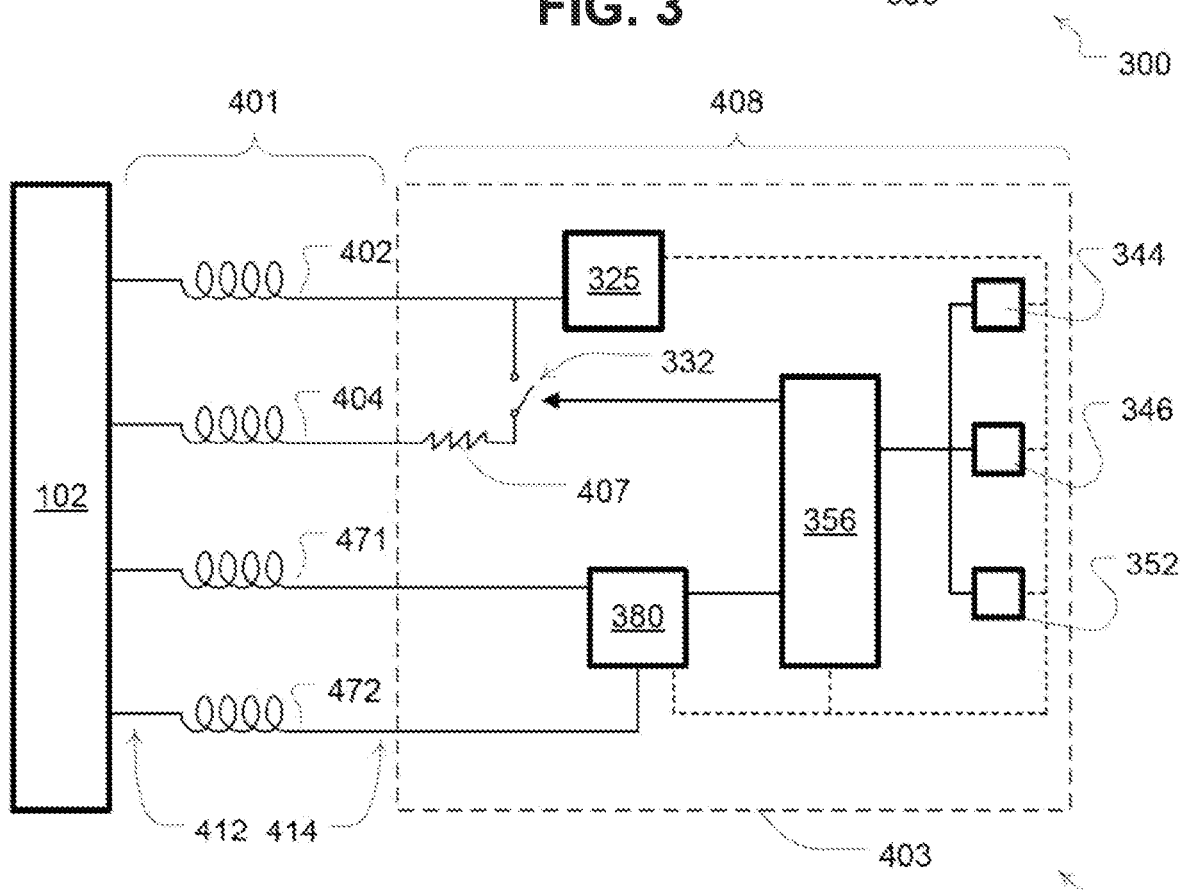
FIG. 4 is a block diagram illustrating a respiratory therapy system including heating and signaling components in a delivery conduit as a non-heated tube version, in accordance with an example of the present technology.

Examples of the delivery conduit for some versions of respiratory therapy system may be considered in relation to the block diagrams of FIGS. 3 and 4. For example, in the diagram of FIG. 3, the respiratory therapy system 300 of FIG. 3 illustrates a gas path of a conduit portion 301, such as a tube or tubing, of the delivery conduit (from the blower end 312 (distal end) to the patient end 314 (proximal end)). A cuff 308 including a delivery conduit control circuit 303 is at the patient end. The gas path of the conduit portion 301 is warmed by heating wires 302, 304, that may be provided in the conduit portion 301. The heating wires 302, 304 may be spiraled around and along the gas path, such as in, on or around the tube. The heating wires 302 and 304 may be insulated electrically and/or thermally, such as by methods and arrangements known in the art.

One of the heating wires 302 receives power from a power supply at the blower end 312 of the conduit portion 301, while the other wire 304 may be coupled to ground at the blower end 312 of the conduit portion 301, thereby completing a heating circuit. In the example of FIG. 3, the wires 302, 304 may also be configured to deliver power from a power supply, such as of the respiratory treatment device, to one or more the components of the delivery conduit control circuit 303 at the patient end 314 of the conduit portion 301. For example, at some point, such as a mid-point, in the heating circuit (e.g., at the patient end 314 of the conduit portion 301), the wires 302, 304 may be connected to a converter 325, such as a DC-DC converter, that converts the incoming power signal to a level suitable for operating the secondary controller 356 of the delivery conduit control circuit 303. Such a converter may also convert the supplied power for powering the delivery conduit sensors 344, 346 and transceiver 352. In some versions, the converter may convert a supplied 12 volt power signal into a 3 volt power signal. Other power signals/conversions may also be implemented. An optional switch 332 may be implemented with the heating circuit for selective control of the supply of power through the heating circuit as previously discussed and discussed in more detail in relation to FIG. 5.

The conduit portion 301 of the respiratory therapy system 300 may also include data bus having two or more additional data bus wires 371, 372 for relaying signals between components at the blower end 312 (e.g., integrated sensors, transceiver, secondary controller) and components at the patient end 314 (e.g., transceiver 352, secondary controller 356). In the example of FIG. 3, wire 371 carries signals to or from a communications interface 380, such as a serial RS232 interface or driver, (which may optionally also be powered by the heating wires—not shown in FIG. 3) interfacing the secondary controller 356 with the controller 120. Wire 372 serves as a ground wire, thereby completing a signaling circuit for the communications with the interface 380.

The example of FIG. 4, the delivery conduit circuit components are similar to that of the version of FIG. 3. However, in FIG. 4, a heating element 407 is added at the cuff 408 of the delivery conduit at the delivery conduit control circuit 403. Thus, the example respiratory therapy system 400 of FIG. 4, the breathable gas that passes through the cuff may be warmed by a heating element 407 (e.g., inductive heater, or other heat dissipater) located within a heated cuff 408 at a patient end of conduit. The conduit portion 401 still includes wires 402, 404, which supply power from a power supply at the blower end 412 to the heating element(s) 407, but may or may not themselves dissipate power along the length of the conduit portion 401 depending on whether the conduit portion includes heating elements or not.

As with the design of the respiratory therapy system 300 of FIG. 3, wires 402 may supply power to other components included in the heated cuff 408, such as components of the delivery conduit control circuit 403 (e.g., transceiver 352, secondary controller 356, converter 325, sensors 344, 346, and/or communications interface 380). Also, as with the design of the respiratory therapy system 300 of FIG. 3, conduit portion 401 may also include data bus wires 471 and 472 for communicating signals between components on both ends of the delivery conduit, such as controller 120 and secondary controller 356.

Although wired power connections are illustrated in FIGS. 3 and 4, in some versions, power of the delivery conduit control circuit(s) may be implemented with contactless power transmission. For example, the delivery conduit assembly may include an inductive connector such as at a patient end and/or a flow generator end. In one arrangement, the tubing assembly may comprise a two wire heating circuit. The circuit may include an end coupler portion, at an end of the delivery conduit, having a wireless power connector. The wireless power connector may then be connected to an accessory, such as a cuff having a delivery conduit control circuit as describe in more detail herein, where the accessory includes a (complementary) connector portion to receive wireless power from the wireless power connector of the delivery conduit. Thus, the accessory or cuff may receive wireless power to power its operations (e.g., sensing, accessory attachment detection and/or identification, wireless communication (e.g. Bluetooth) for communication (e.g., with the respiratory therapy device) of data, such as from its sensors or component detectors, etc.

Figure 5:
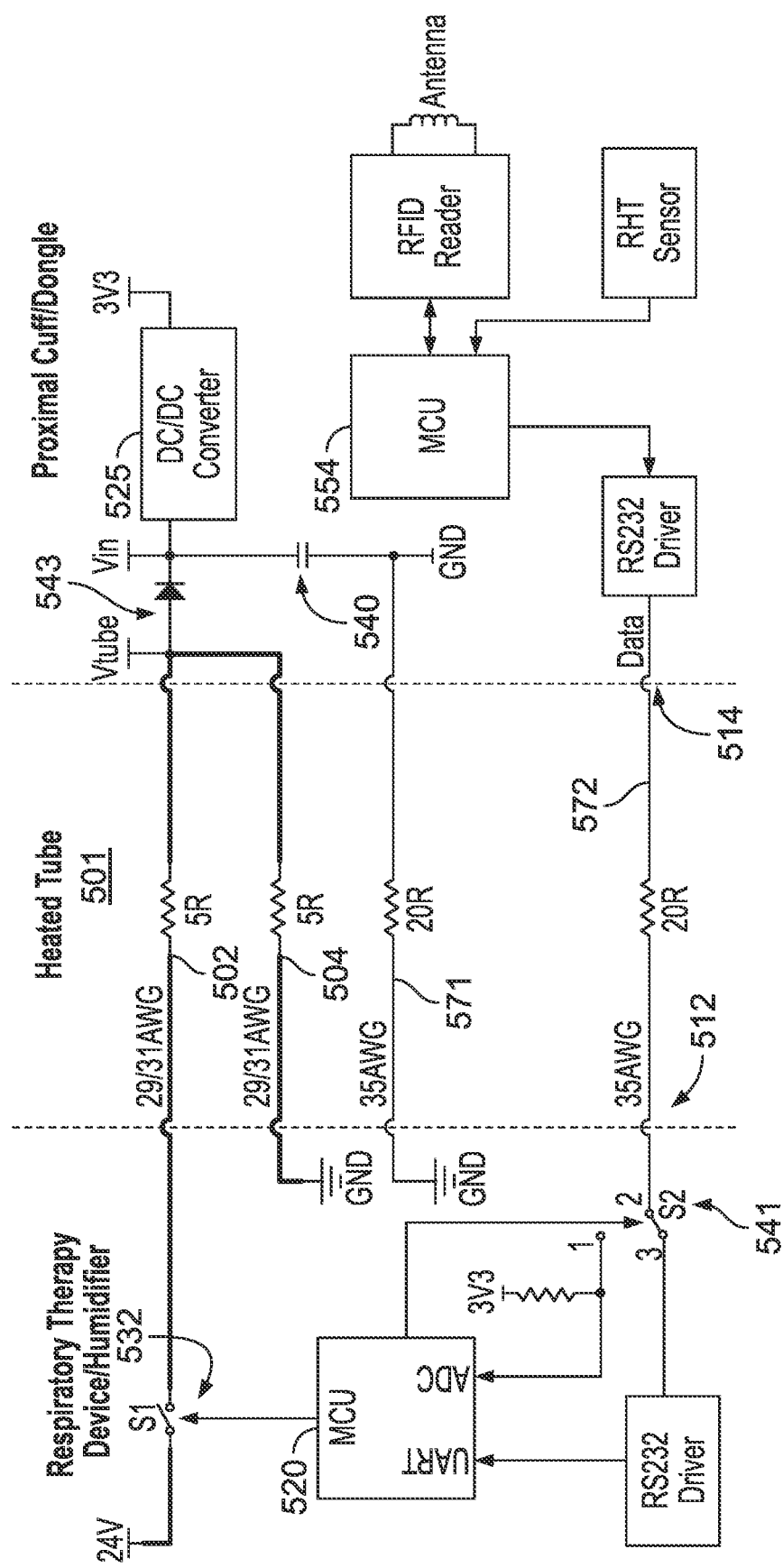
FIG. 5 is a circuit diagram illustrating a respiratory therapy system including heating and signaling components in a delivery conduit having a heated tube, in accordance with an example of the present technology.

As previously discussed, such as in relation to the wiring of FIGS. 3 and 4, heating and signaling may be controlled by a controller 120 connected near the blower end of the delivery conduit. In this regard, FIG. 5 further illustrates an example control application for the system 300 of FIG. 3, which can be similarly applicable to the system 400 of FIG. 4. In the diagram of FIG. 5, the blower end 512 of the conduit may be coupled to a respiratory therapy device 102 that includes a switch 532 for controlling heating operations through the conduit portion 501. A controller 520 (such as a microcontroller or microprocessor unit) is operatively coupled to the switch 532 and may be implemented to control the timing of the heating operations.

Figure 5A:
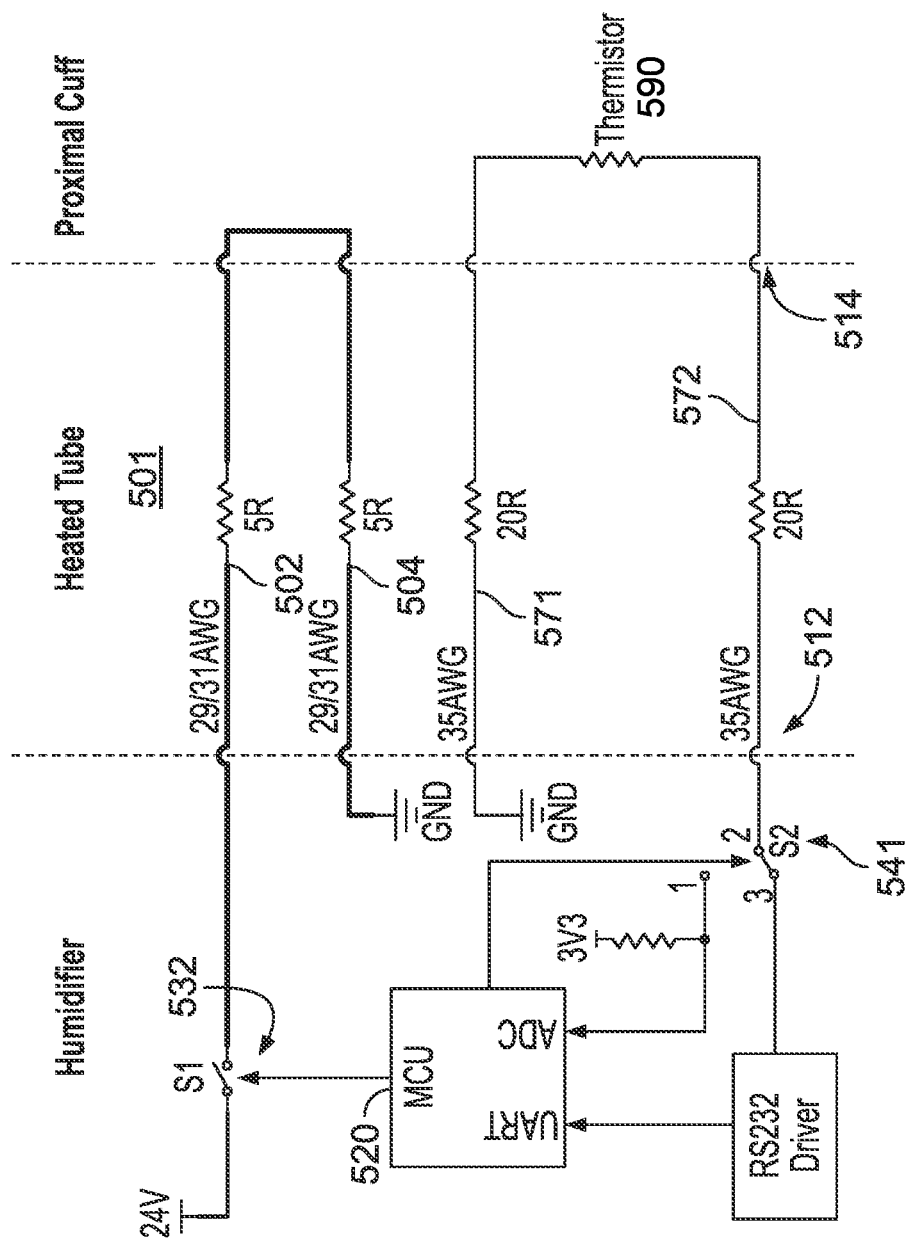
FIG. 5A is another circuit diagram of an example of the present technology with an NTC thermistor in a cuff.

In the example of FIG. 5, an optional load capacitor 540 is coupled to the heating wires 502, 504 in order to maintain charge even when the switch 532 is open. Charging of the capacitor may be implemented from the wire 502 through a diode 543, which can be arranged to permit current flow from the wire 502 only in the forward direction of the converter and capacitor. Thus, when the switch 532 is open, the load capacitor 540 may continue to provide energy (e.g. a charge) to the DC-DC converter 525, and not the reverse direction to the wires 502, 504, in order to continuously power the patient-end components (e.g., temperature sensor 544, humidity sensor 546, and RFID reader 552). In the version illustrated, an optional switch 541 in the control circuit of the respiratory therapy device 102, under control of the controller 520, may be selectively controlled so as to either (a) receive communications through a communications interface at the controller 520 or (b) to receive a sensor signal at controller 520, both via the wire 572. In this regard, an analog sensor signal proportional to a sensor (e.g., any of the provided sensors such as a temperature and/or humidity sensor) reading/measurement may be provided on the wire 572 from the cuff circuitry for sampling by the controller 520 at an analog-to-digital (ADC) input sampler(s). Alternatively, a data signal may be provided from the cuff circuitry on the wire 572 for receiving by a signaling interface of the controller 520 (e.g., via an RS232 driver and universal asynchronous receiver/transmitter input of the controller 520.) According to one aspect, the switching 532 may allow different types of cuff configurations to be connected, such as those shown in FIG. 5 and FIG. 5A. FIG. 5A shows another example arrangement of the present technology comprising an NTC thermistor 590 in the cuff.

Operations of the circuits of FIG. 5 may be considered in reference to the signaling graphs of FIG. 6, which illustrate an example scheme for intermittent control of the heating and signaling operations that may be implemented by the controller 520, such as by selective operation of switch 532. For clarity, the vertical axis represents amplitude, and the horizontal axis represents time. Curve 610 shows voltage verses time along heating wire 502. In effect, this demonstrates operation of the switch 532, in which power is cyclically provided to and cut off from the heating wires 502, 504. Operation of the first switch may be a pulse width modulation, in which the controller 520 controls the duty cycle of the switch. Curve 620 shows the voltage verses time provided to the converter 525, which in part is supplied by the load capacitor 540 during the tube off cycle. In this regard, charge from the load capacitor 540 is maintained at a relatively constant level, allowing for the converter 525 to maintain a sufficient constant output voltage (shown at curve 630) for continued operation of the patient-end components (e.g., second controller 554 etc.).

Curve 640 of FIG. 6 shows an example voltage verses time plot of signaling wire 572 which provides data transfer between the controller 520 and second controller 554. In the example of FIG. 6, data may be continuously transmitted from the patient-end secondary controller 554 to the blower-end controller 520. Thus, the wire 572 in this version may be implemented solely for data communications. However, in other examples discussed herein, additional switches may be provided to control when signaling operations occur.

Figure 7:
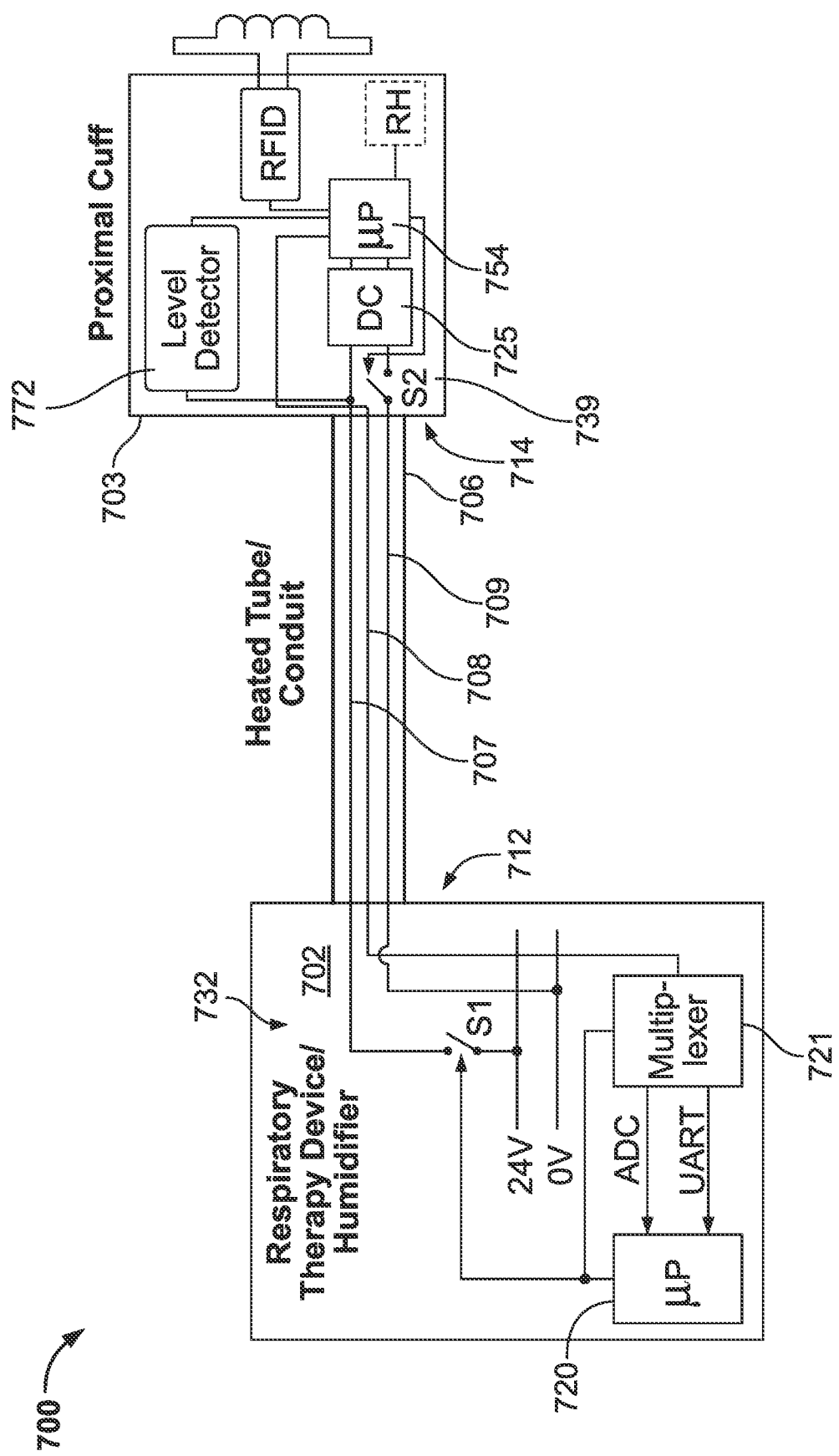
FIG. 7 is another block diagram of a system having heating and signaling components sharing a common ground wire of a delivery conduit as a heated tube version, in accordance with an example of the present technology.

One example in which it may be advantageous to control the timing of signaling operations is shown in FIG. 7. In this version, the heating and signaling operations may time share a common wire, such as a ground or return wire. Thus, in some versions fewer wires may be implemented. In the example of FIG. 7 three wires may be implemented for both the signaling and heating operations of the conduit such that one of the wires may be intermittently engaged for completing the signaling and heating alternatively. In FIG. 7, an example respiratory therapy system 700 includes a respiratory treatment device 702 (e.g., such as a flow generator with or without a humidifier) for providing breathable gas to a patient (not shown) through a delivery conduit 706. The breathable gas is warmed in the delivery conduit by a heating element of wire 707, such as those described above. The patient-end 714 of the delivery conduit 706 also includes a secondary controller 754 that communicates with a controller 720, such as through a switch or multiplexer 721, at the blower-end 712 of the delivery conduit 706 over a data bus wire 708. A common ground wire 709 is provided in the delivery conduit 706 to alternatingly complete the heating circuit of the heating wire 707 and the signaling circuit of the data bus wire 708. In this manner, only one of a heating operation and a signaling operation may be performed at a given time.

In order to control the heating and signaling operations in this version, each of a first switch 732 and a second switch 739 are provided in the respiratory therapy system 700. The first switch 732 is located in the respiratory therapy device 702 at the blower-end 712 of the delivery conduit, and its activation is selectively controlled by the controller 720. The first switch 732 is similar in operation to that of switch 532 of FIG. 5. It operatively couples and decouples wire 707 to a high or positive side of a power supply (e.g., 24 volts). The second switch 739 is located in the delivery conduit such as in the delivery conduit control circuitry 703 of the cuff of the delivery conduit. The activation of the second switch 739 is selectively controlled by the second controller 754. The second switch 739 is operatively controlled to couple and decouple the proximal end of wire 707 to ground wire 709. When so coupled, a heating operation can occur due to completion of the heating circuit when wire 707 is powered. At this time, power to the converter 725 is shorted, thereby temporarily denying power supply to the converter. When the proximal end of wire 707 and the ground wire 709 are decoupled by the second switch 739, the heating circuit is broken and in this condition the converter can be powered by the power supply when wire 707 is powered. During this latter condition, the signaling circuit of wires 708, 709 may be completed for signaling by the signaling operations of the microcontroller 720.

Figure 8:
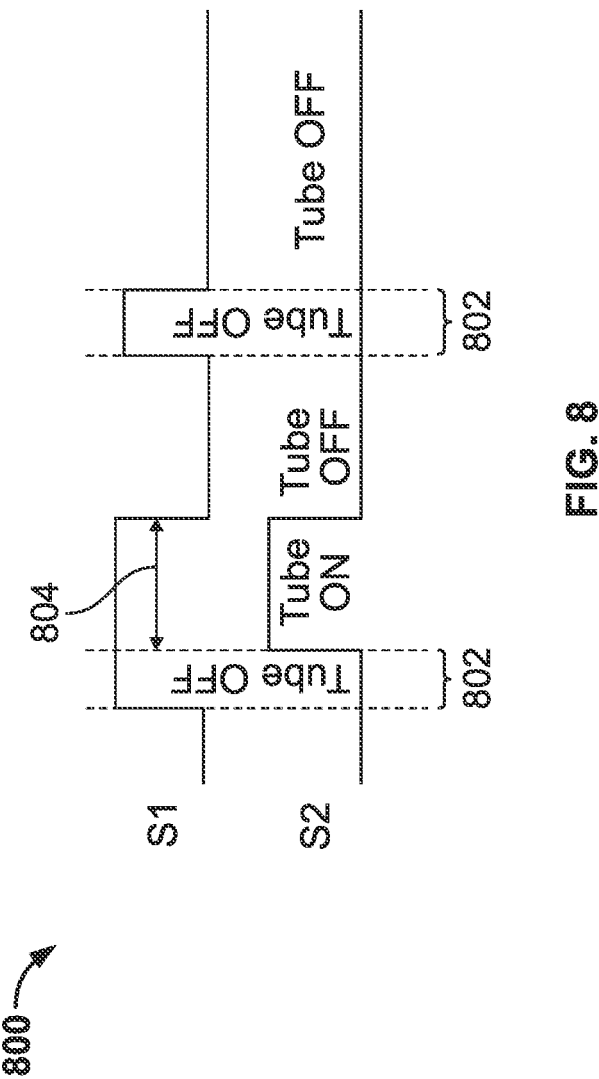
FIG. 8 illustrates an example control scheme for the system shown in FIG. 7.

Thus, one or both of the controller 720, 754 may be configured to interleave the heating and signaling operations, such as in alternating fashion, such that these operations alternate so as to avoid a simultaneous heating control operation and a data communication control operation. An example signaling control scheme 800 for such interleaving employing the components of FIG. 7 is illustrated in FIG. 8, in which operation of the first switch S1 (e.g., first switch 732 of FIG. 7) and operation of the second switch S2 (e.g., second switch 739 of FIG. 7) are shown.

The interleaved operations may be cyclical but may be considered to begin with a blanking window 802. During a blanking window, the controller 720 controls operation of the first switch to close to allow supply of power to the heating wire 707. During this blanking window 802, the secondary controller controls operation of the second switch to open (so as not to complete the heating circuit). During such a blanking window, power supplied over heating wire 707 is applied to the converter 725, thereby powering the patient-end sensors and secondary controller 754. Moreover, during such a blanking window, the wire 709 is available to complete the signaling circuit, which in turn allows for signaling to occur between the patient-end and blower-end sensors and controllers. The blanking window thus permits signaling and may last a predetermined amount of time and may be periodically repeated.

After the blanking window, a heating window 804 may begin. During the heating window, the controller 720 continues to control the first switch to apply power to the wire 707. During the heating window, the secondary controller 754 also controls the second switch 739 to activate the heating operation by closing so as to couple wire 708 and wire 709 at the second switch 739. In this regard, the secondary controller 754 can control the desired time period for heating by controlling the second switch. For example, when the second switch is closed/on (heating operations occur) and when the second switch is open/off (heating operations suspend). The longer the second switch is maintained in the closed position, the longer the heating circuit is completed and the more heat is transferred to the breathable gas of the delivery conduit. In other words, when both switch S1 and switch S2 are on, heating operations occur. When switch S1 is on and switch S2 is off, information signaling can occur. The controllers may operate these switches by various signaling schemes, such with pulse width modulation, for permitting the interleaved heating and signaling operations.

For example, the controller 720 may generate pulse width modulation signals to control of the first switch to activate the heating and signaling cycles. In some cases, the second controller 754 may generate pulse width modulation signals to control of the second switch to interleave heating and signaling cycles. Such signals may be continuously repeated. Thus, the interleaving operations may be performed by the second controller at a predetermined and fixed frequency. However in some cases, the interleaving may be more dynamically implemented, such as in relation to a condition detected by the second controller 754, such as in relation to measurements made by one or more of the sensors of the delivery conduit control circuit and/or a determination made with its transceiver.

A level detector 772 is used to obtain the status of switch S1 in respiratory treatment device 702. In the example arrangement shown in FIG. 7, the level detector allows synchronization of S2 with S1. Note also that DC to DC converter 725 may be understood as an implementation in which the diode 543 and capacitor 540 shown in FIG. 6 are included in converter 725.

Figure 9:
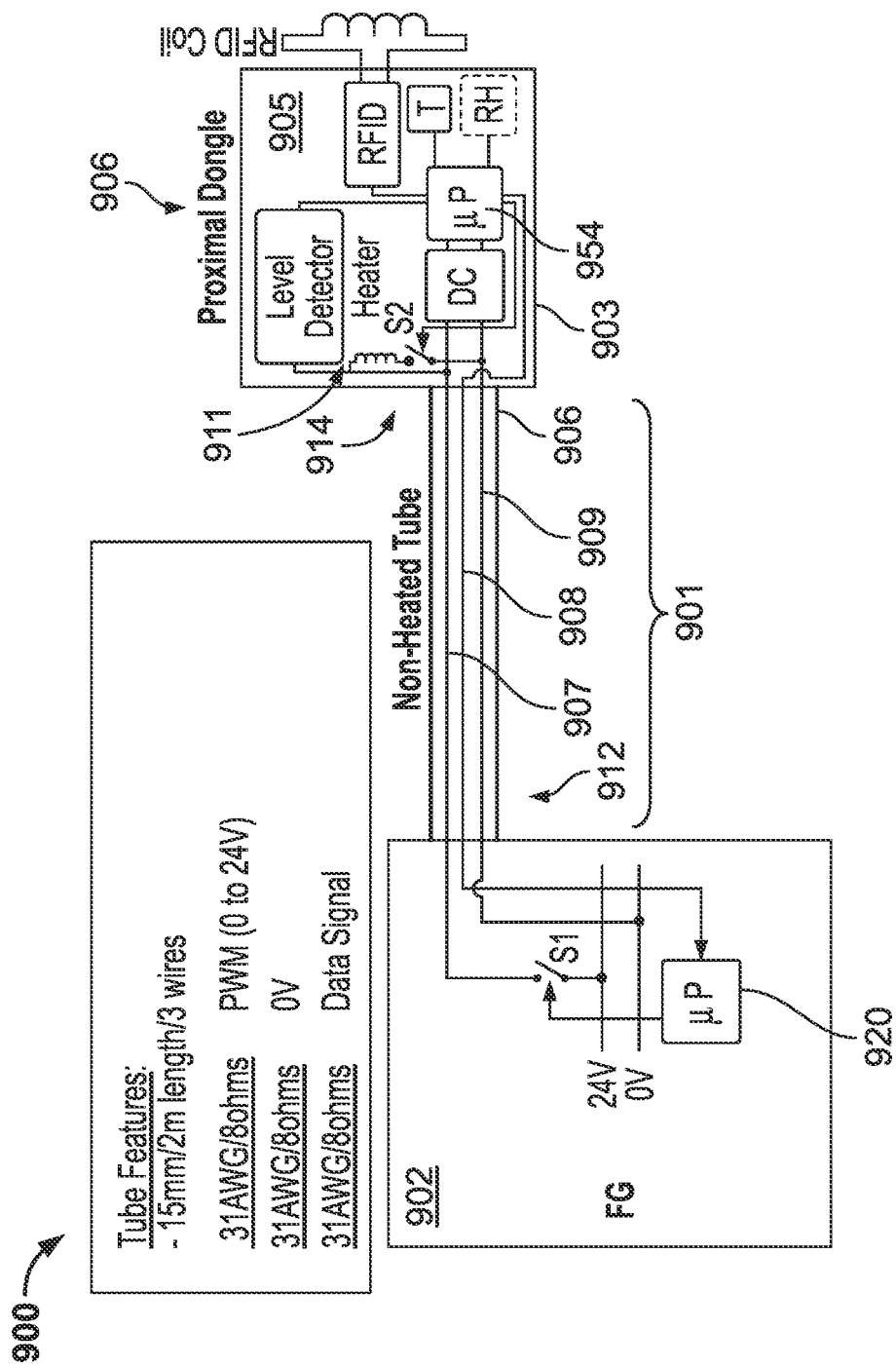
FIG. 9 is another block diagram of a system having illustrating heating and signaling components sharing a common ground wire of a delivery conduit as a heated tube version, in accordance with an example of the present technology.

Another example respiratory therapy system 900 may be considered in relation to FIG. 9. This example includes components similar to those of the version of FIG. 7. In this example, the delivery conduit portion 901 may optionally omit a heating element. Moreover, in this version a heating element may be located with the delivery conduit control circuit 903 located within the heated cuff 905 at a patient end of a delivery conduit 906. Thus, the breathable gas traversing through the delivery conduit can be warmed by a heating element 911 (e.g., heat dissipater) located within a heated cuff 905 at a patient end of a delivery conduit 906. Similar to FIG. 7, the system includes a controller 920 in a respiratory treatment device 902 and a secondary controller 954 included in the cuff 905. These devices may control operations so as to interleave heating and signaling operations in relation to the heating wire 907, and signaling wire 908, and a common wire 909 (ground) through the conduit portion 901. The same or similar interleaving scheme discussed in connection with FIGS. 7 and 8 may be utilized in the system 900 of FIG. 9.

Figure 10A:
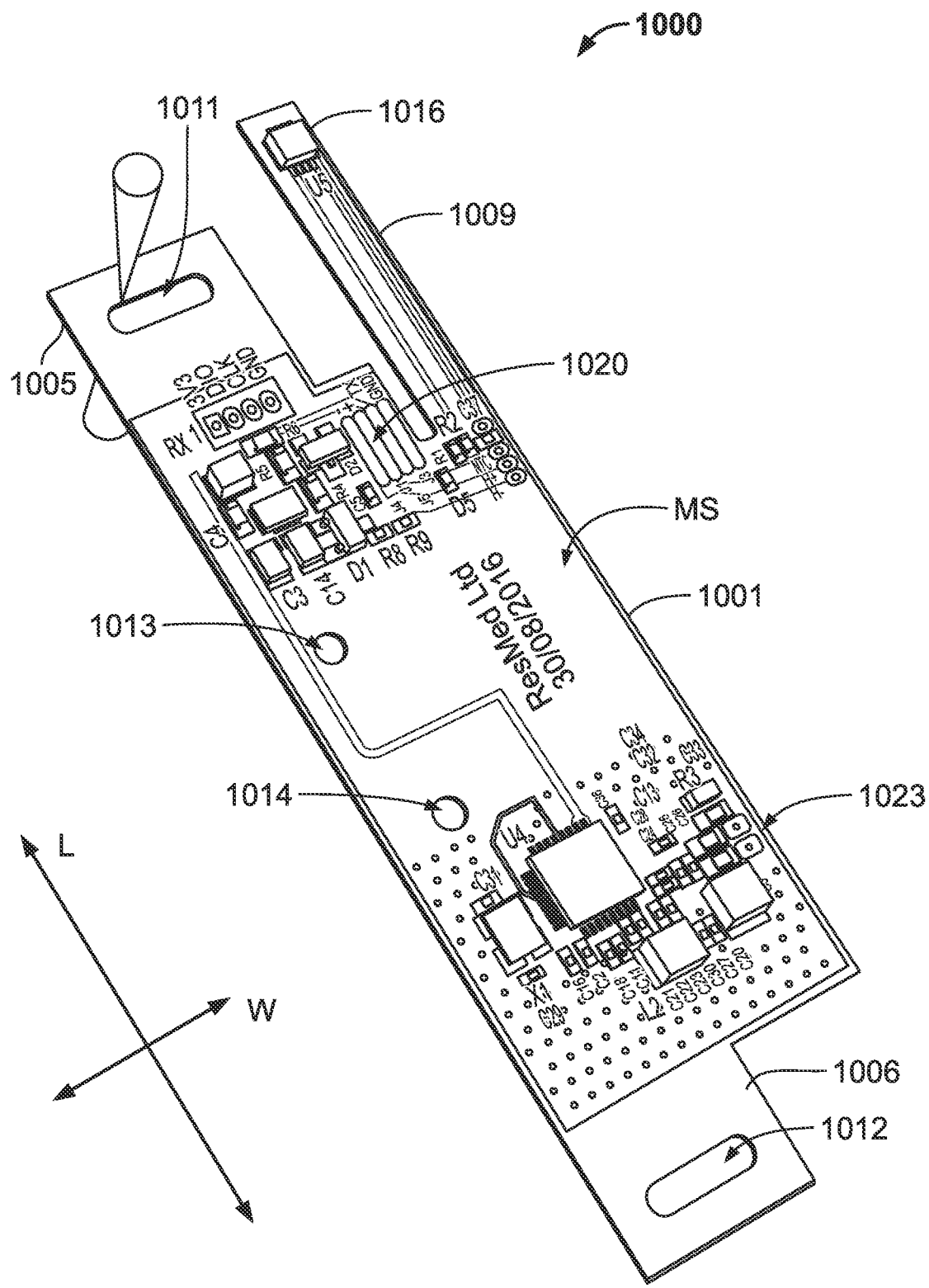
FIGS. 10A and 10B are perspective illustrations showing views of an example printed circuit board for use in any of the above examples.
Figure 10B:
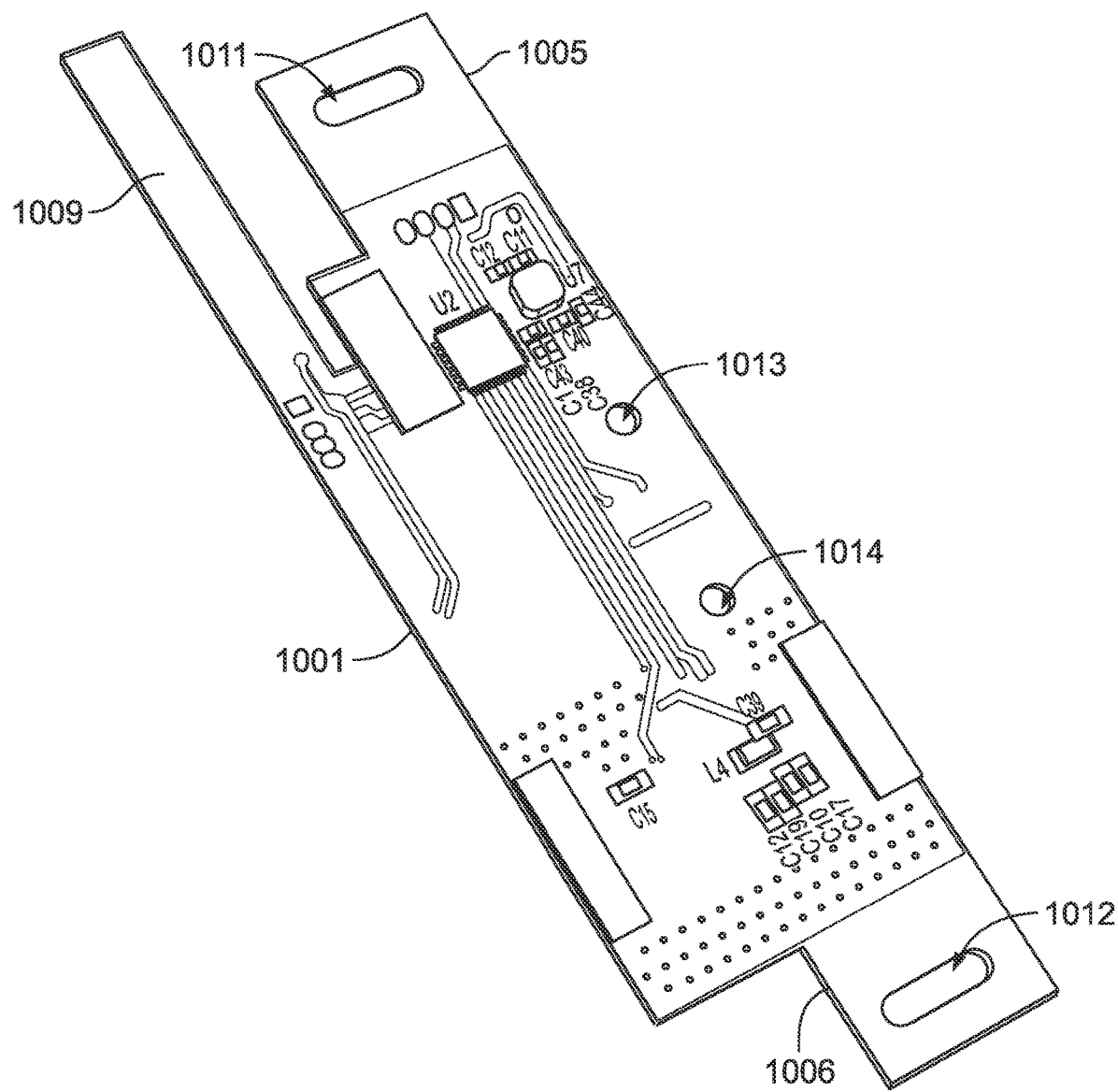

The above example systems include several patient-end components (e.g., delivery conduit control circuit) of a delivery conduit 106 that may be formed of discrete circuit element. However, in some versions thereof, the circuit elements may be integrated in a single module, such as a printed circuit board. An example of such an integrated circuit board may be considered in relation to the illustration of FIG. 10. In this regard, FIGS. 10A and 10B show opposing surface side of an example circuit board 1000 that may be adapted to be flexible so that it may conform to a shape of an exterior of a delivery conduit comprising an air path therethrough. For example, the circuit board 1000 may be configured to bend or curve around a substantially cylindrical (e.g., mostly cylinder shaped, mostly oval shaped etc.) delivery conduit. Thus, such a circuit board may be made of a flexible material. Its length may be configured so that the board can be wrapped or bent around all or most of the perimeter or circumference of a delivery conduit. In some instances, the circuit layout of the board and its materials may be arranged to permit bending along a lengthwise axis L, but to remain rigid along a widthwise axis W. Such a design can permit its insertion within a smaller housing while still protecting the electrical elements of the board.

The circuit board may include components of any one or more of the delivery conduit control circuits previously described. For example, it may include one or more of: a microcontroller or microprocessor unit, one or more sensors (e.g., for detecting/measuring a property of the breathable gas passing through the delivery conduit, such as its temperature or humidity), and a wireless transceiver (e.g., for communicating with a controller of a flow or pressure generator, for communicating with an identification tag located in a patient interface). These components may be mounted to the circuit board.

The circuit board may include a main body portion 1001 with a first surface MS on which all or some of the above-described components are integrated. Extending in the lengthwise direction L from both ends of the main body portion may be a pair of mounting tabs 1005 and 1006. Each mounting tab may extend most of the widthwise direction L of the main body portion. The circuit board may include an extension strip 1009 on which at least one of the sensors may be mounted. The extension strip 1009 may extend in the lengthwise direction L, and may extend further than even the adjacent mounting tab. The extension strip 1009 may be adapted to extend into an air path defined by the delivery conduit through which breathable gas flows. Thus, the sensor(s) 1016 mounted on the extension strip may be exposed to, or located close to (e.g. separated only by a protective housing) the flow of the breathable gas and to sense a characteristic thereof, such as temperature or relative humidity, from within the gas passage of the delivery conduit. The extension strip 1009 may be located at an end of the circuit board, and may be laterally adjacent to a mounting tab.

The circuit board may also include terminals 1020 to which the heating, signaling, and ground wires extending along the delivery conduit may be coupled or attached (e.g., soldered). In one example, the terminals may connect to a data bus port for communication information between the integrated components of the circuit board and the controller 120 of the respiratory therapy device 102. The terminals may additionally connect to a power line for receiving power to charge the components of the circuit board. The circuit board may also include terminals 1023 for attachment to an antenna, such as an RFID antenna. The terminals 1023 may be configured to connect to a transceiver, such as an RFID or NFC transceiver (such as the transceiver 152 described in relation to FIG. 1). For example, an RFID coil may be attached to the terminals 1023.

The circuit board may also include holes or grooves to facilitate fixing or securing the board to the delivery conduit housing when wrapped about to a portion of the delivery conduit. For example, such hole may couple to a post structure of a cuff housing of the delivery conduit. In the example of FIGS. 10A and 10B, each of the tabs 1005 and 1006 includes a respective hole 1011, 1012. The main body portion of the circuit may include additional holes 1013, 1014, which may be aligned, lengthwise, with holes 1011 and 1012.

In the example of FIGS. 10A and 10B, the outline of the main body portion of the circuit board is substantially rectangular in shape. However, in other examples the surface of the main body portion may have a different shape. For instance, a middle portion of the surface of the main body portion may be tapered to have a narrower width than the remainder/ends of the surface of main body portion. Thus, the surface of the circuit board may be an hourglass shape.

Figure 11:
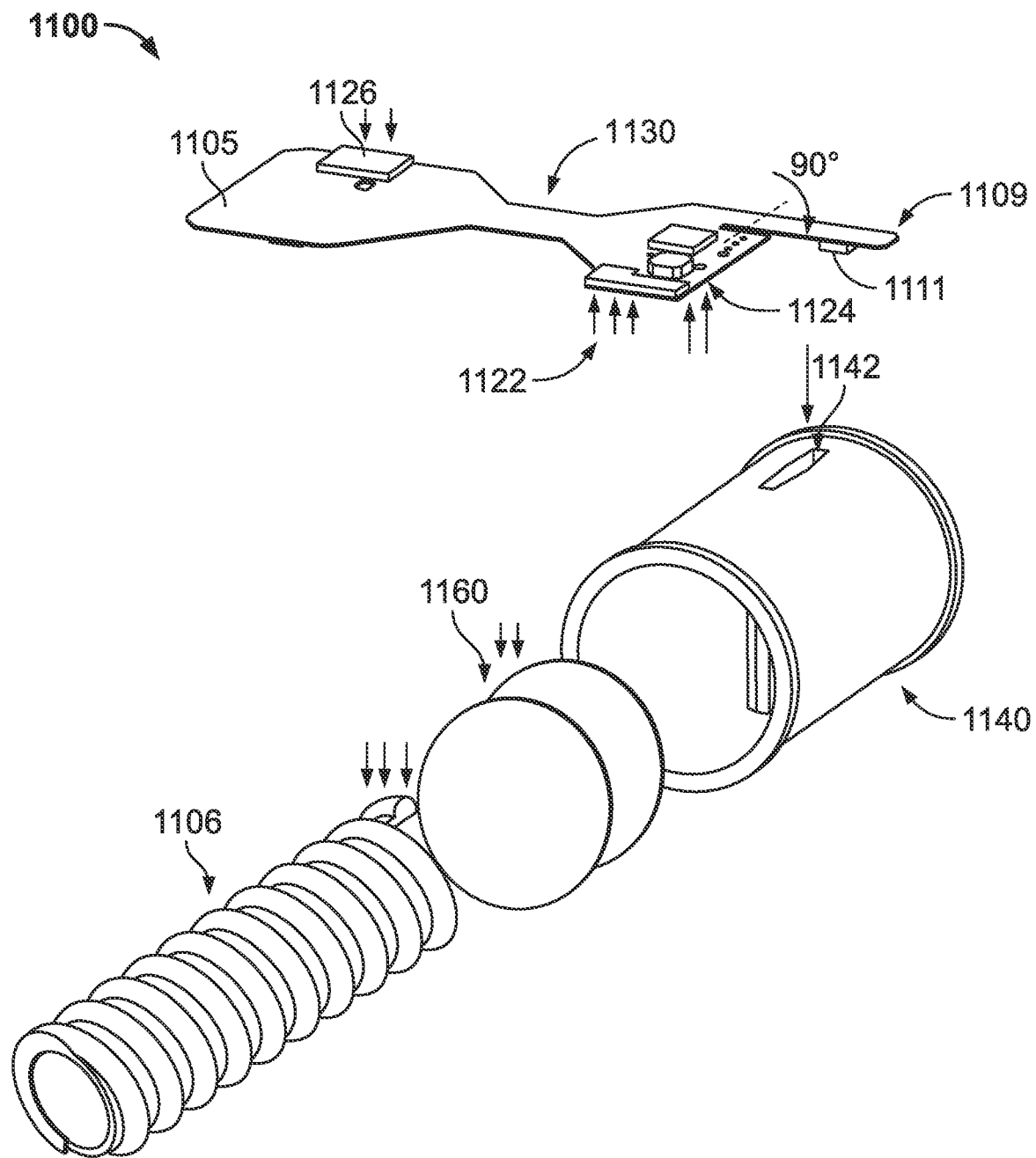
FIG. 11 is an exploded perspective view of an example assembly for a delivery conduit for a respiratory therapy system in accordance with an example of the present technology.

FIG. 11 illustrates a portion of an example of such a flexible circuit board of an hourglass shape in relation to an exploded view of the components of a delivery conduit assembly. The flexible circuit board 1105 also includes an extension strip 1109 comprising a sensor, such as a relative humidity and temperature (RHT) sensor 1111 and configured to be bent to place in the path of the breathable gas. For example, the extension strip 1109 may be configured to bend approximately ninety degrees for insertion into the air passage of the cuff. In the example, a delivery conduit assembly 1100 includes the circuit board 1105, which may be wrapped around the delivery conduit at or near a patient-end of the delivery conduit. In the example of FIG. 11, the delivery conduit assembly 1100 includes a hollow cylindrical cuff 1140 that may serve as a dongle. The cuff 1140 may have one or more structural mounting features (e.g., tabs, projections, slots, etc.), such as aperture 1142 to receive there through the extension strip 1109 of the circuit board, on an outer surface thereof. The mounting features of the cuff may be adapted to align with and to the complementary mounting features of the circuit board, for example to extend through the respective holes positioned on the circuit board, such that the circuit board may be affixed to the cuff. The cuff 1140 may be integrally connected to a tube portion 1106 of the delivery conduit, such as by overmoulding, or be configured to be removably coupled to the tube portion 1106. In one example, the cuff 1140 may comprise features in its inner surface (e.g., shaped and sized complementarily to the tube portion) adapted to receive the tube portion 1106.

The example of FIG. 11 shows a cuff comprising (e.g., adapted to enclose) a heating element or evaporator 1160, particularly an evaporator, such as when the cuff serves as a heated cuff of the delivery conduit. The evaporator 1160 (shown as heating element 911 in FIG. 9) has a diameter roughly equal to the inner diameter of the cuff, such that any breathable gas that flows through the cuff from the central flexible hose portion of the delivery conduit 1106 to the patient interface may be heated by the evaporator. In one example, a humidification system such as one described in the PCT Patent Application PCT/AU2017/050912, the entire disclosures of which is incorporated herein by reference, may be suitable for use with the evaporator 1160 shown in FIG. 11.

In one example, the printed circuit board 1105 may include a set of terminations 1122 for connecting to the wires 1004 of the delivery conduit (e.g., wires 707, 708, 709 of FIG. 7), and a set of terminations 1124 for connecting to the leads (e.g., high side and low side) of the evaporator to power the evaporator. Another set of terminations 1126 are provided for connection to an RFID coil. As illustrated in FIG. 11, the heating/signaling/ground wires of the set of wires of the delivery conduit are wrapped or molded to an outer perimeter of the tube portion, such as in its helical rib. In the example of FIG. 11, the outside diameter of the cuff is in a range of approximately 25 to 35 millimeters such as about 30 millimeters. In some versions, the cuff may have an outer diameter in a range of about 22 mm to about 25 mm. In other versions, such as for example a Dongle design, an outside diameter of 30 mm may prove suitable. In addition, for a Dongle design an extended flexible bridge portion 1130 may be implemented to allow for different Dongle diameters.

As such, the cuff may then serve as a coupler for removable connection of the delivery conduit to a patient interface. In some versions, the inner surface of the cuff may define a tubular space through which air flows from the delivery conduit to the patient interface. The outer surface may also be substantially concentric to the inner surface. The cuff may further comprise a hollow space therebetween, and the printed circuit board (and components mounted thereon) may be disposed in the hollow space. For example, the cuff may comprise an outer casing or sheath portion, for example molded to form a protective layer (e.g. to form a water ingress seal) over the cuff mounted circuit board so as to protect the circuit board (e.g. from human contact or accidental damage) during use. In some such versions, the sheath or outer casing may be a TPE or silicone overmould. The sheath can protect the electrical components of the cuff but may also serve to seal the cuff from the potential for any air/gas leaks from inside the cuff such as when the cuff includes apertures, slots or other channels to permit wiring or mounting of the circuit board. The outer sheath portion may also provide a convenient, high-friction gripping surface for a user.

In some versions, the cuff may be configured with additional components, for example, the cuff may include a heat and/or moisture exchanger and/or vent. For example, any of the exchangers described in U.S. Patent Application Publication No. US-2014-0305431, the entire disclosure of which is incorporated herein by reference, may be included in the cuff. By way of further example, any of the vents described in U.S. Patent Application Publication Nos. US 2014/0283831 and US 2014/0069428, the entire disclosures of which are incorporated herein by reference, may be included in the cuff.

Figure 12:
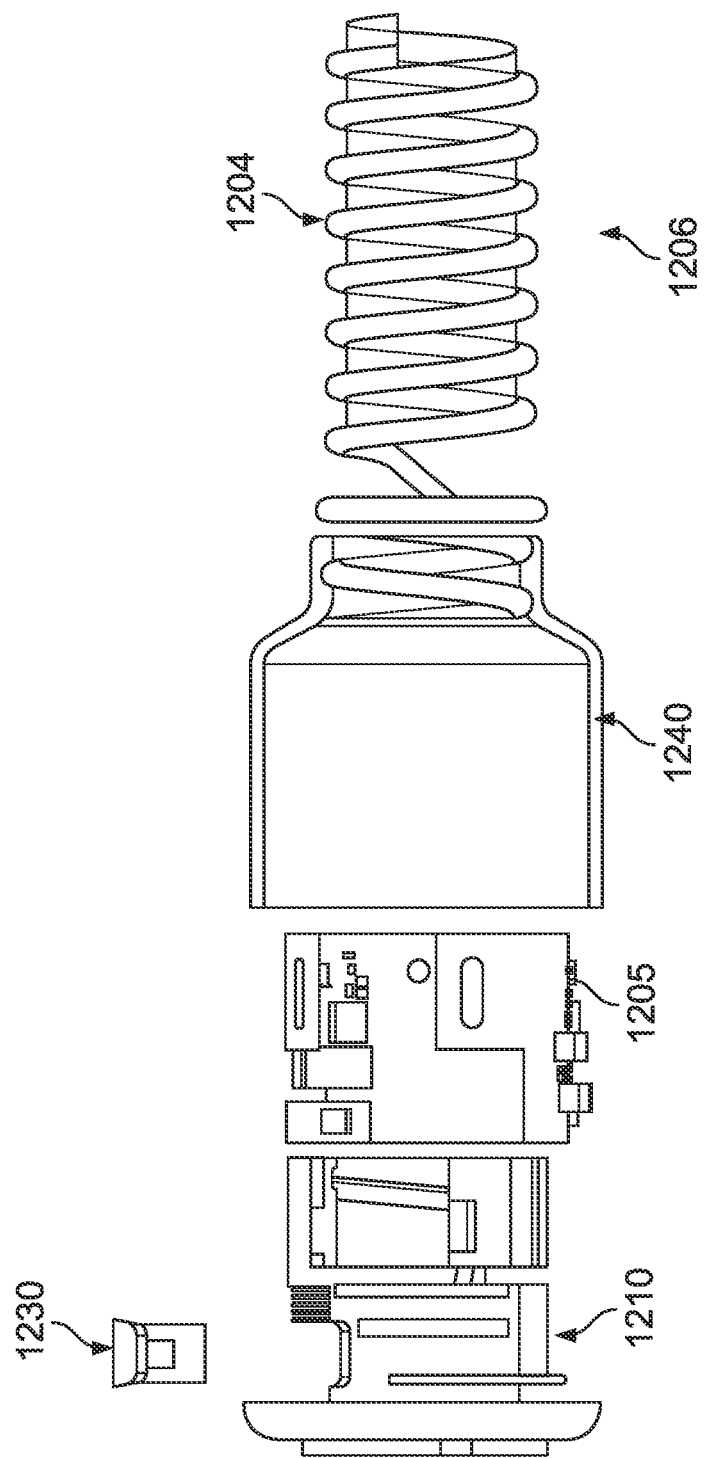
FIG. 12 is an exploded side view of an example modular assembly for a delivery conduit of a respiratory therapy system in accordance with an example of the present technology.

Another version of an example delivery conduit 106 is illustrated in FIG. 12. The figure shows a portion of the conduit in an exploded view with several components. In this version, the delivery conduit includes a hollow tube portion 1206 having one or more wires 1204 (e.g., wires 707, 708, 709 of FIG. 7 or wires 302, 304, 371, 372 of FIG. 3) helically or spirally wrapped around its outer circumference. Such a configuration of wires in relation to the delivery conduit may be considered a rib. The assembly also includes a delivery conduit connector end 1210 (or end portion of a cuff) adapted to be fixed to an end of the hollow tube. The assembly also includes a printed circuit board 1205 such as any of the delivery conduit control circuits previously described. In this version it is adapted to be flexibly wrapped around an outer surface of and affixed to the delivery conduit connector end 1210. In this version, the assembly also includes a sensor case 1230. The sensor case covers a sensor for protection. In this regard, the sensor case may cover a sensor of the printed circuit board that extends through an opening in the delivery conduit connector within the gas passage/path of the delivery conduit connector. Such a sensor may be a sensor on the extension strip 1009 shown in FIG. 10A. Thus, the sensor case 1230 may be within the gas passage of the cuff. The assembly of FIG. 12 also includes a sheath or outer casing 1240, such as an over-mold, for encasing all or part of the above-mentioned assembly components associated with the cuff. In some forms, the outer casing 1240 may comprise multiple molded components which are assembled together to encase all or part of the above-mentioned assembly components associated with the cuff. Advantageously, use of a flexible circuit board may simplify the manufacturing process, and reduce a size of the delivery conduit 1206, by allowing the electronic components to be compactly packaged around a periphery of the delivery conduit 1206, while an operator (or an automated process) may simply wrap the flexible circuit board.

Assembly of the delivery conduit of FIG. 12 may be considered in relation to FIGS. 13A-13F. These figures illustrate one example of features and steps for bringing together the components. While the steps are shown in a particular order for discussion purposes, it will be understood that some steps may be may be omitted, additional steps may be added, and certain steps may be performed either simultaneously or in a different order.

Figure 13A:
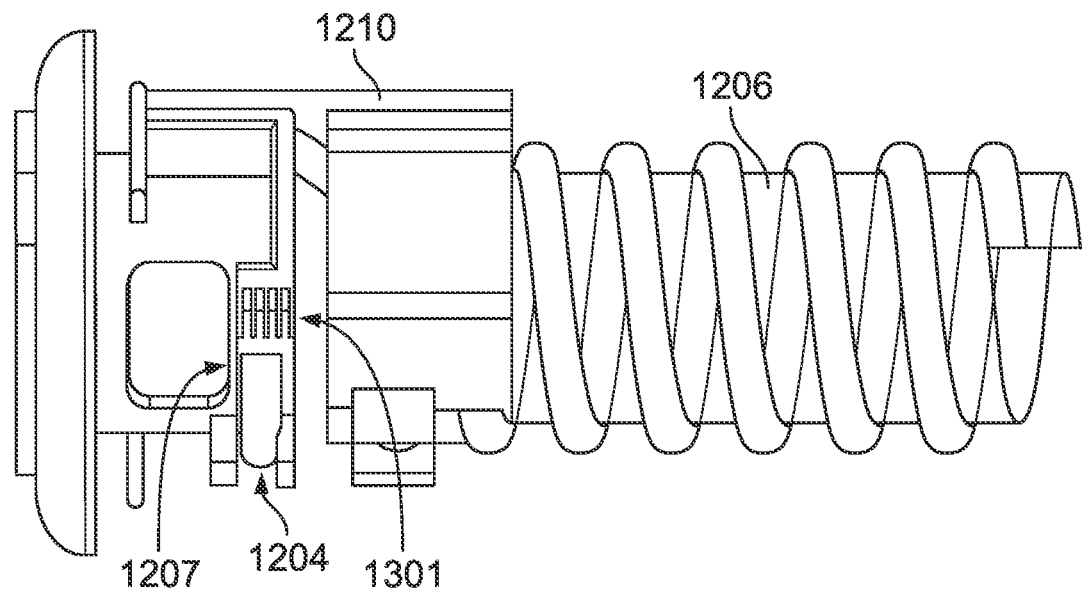
FIGS. 13A-13F illustrate portions of the delivery conduit modular assembly of the FIG. 12 in various stages of assembly.

In FIG. 13A, the hollow tube portion 1206 is inserted into the delivery conduit connector end 1210. The hollow tube is configured so that the rib 1207 comprising wires 1204 can be inserted into slots 1301 of the delivery conduit connector end. For example, each slot may hold one wire. For example, four slots may be included in the connector end or cuff. Such alignment slots position the wires to permit ready connection of the ends of the wires with the terminals of the circuit board when the board is added.

Figure 13B:
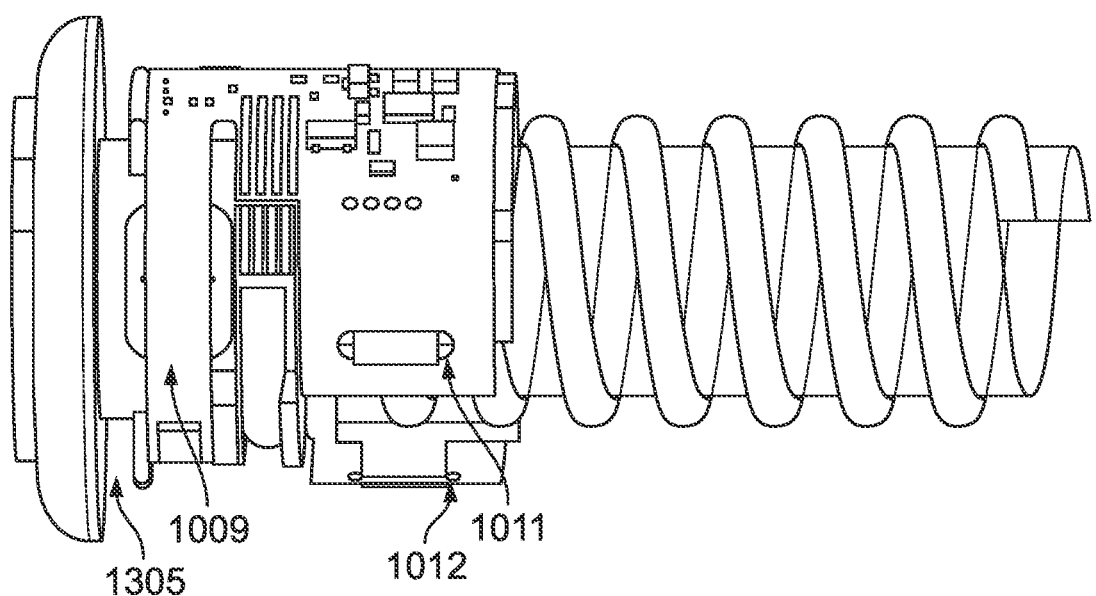

In FIG. 13B, the printed circuit board 1205 is wrapped around the outer circumference of the delivery conduit connector end 1210. The wires 1204 may be soldered/welded to the appropriate terminals of the circuit board (e.g., terminals 1122 of FIG. 11 or 1020 of FIG. 10A). Also, an antenna (not shown), such as an RFID coil, may be connected/welded/soldered to a transceiver module of the circuit board. The antenna may be wound around the outer perimeter of the delivery conduit connector end in an antenna slot 1305 between the delivery conduit connector end 1210 and the printed circuit board.

Figure 13C:
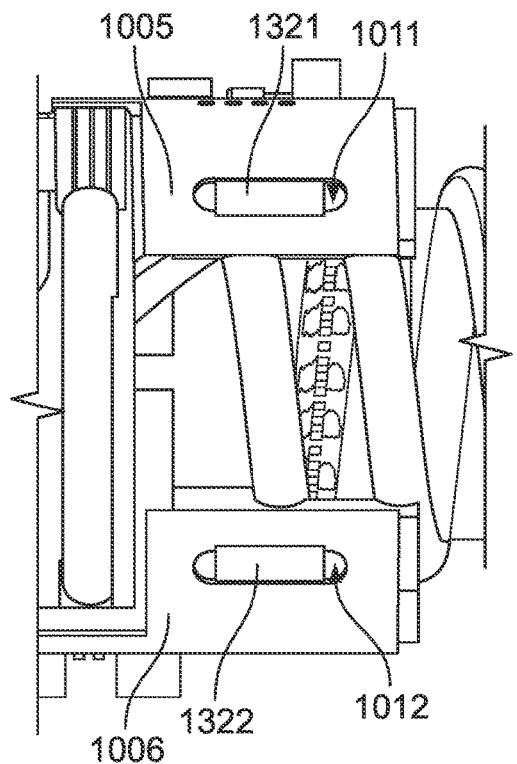

FIG. 13C shows the printed circuit board and delivery conduit connector end from an opposing side view relative to FIG. 13A. In FIG. 13C, slots 1011 and 1012 of the printed circuit board (see also FIG. 13D) are shown to clip together with projections 1321 and 1322 of the delivery conduit connector end 1210. Thus, the board may be wrapped or rolled around the delivery conduit connector end to engage the slots and projections for securing the board to the cuff. In some versions, when included, the extension strip 1009 of the circuit board (shown in FIG. 13B) may first be inserted in a sensor aperture of the delivery conduit connector end before flexibly wrapping the board around the cuff/delivery conduit connector end. Such a wrapping bends the extension strip. The sensor aperture permits the extension strip 1009 and its sensor to extend through the connector end and into the gas passage of the delivery conduit connector end.

Figure 13D:
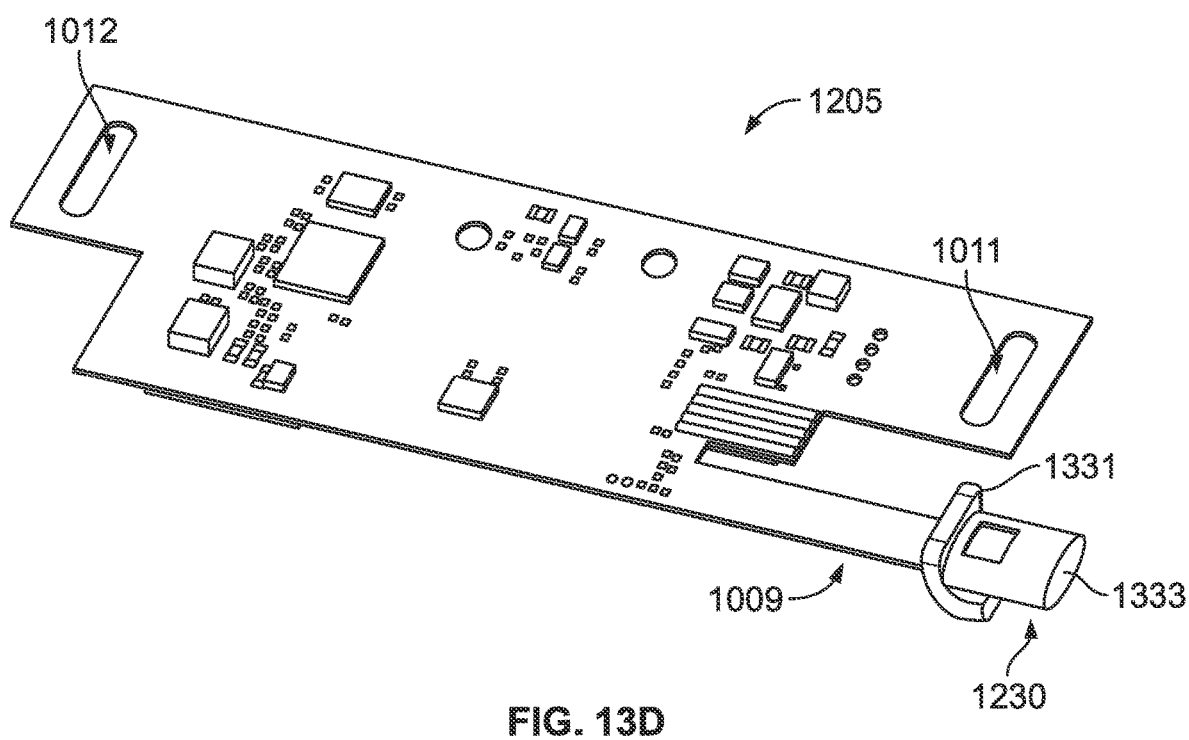
Figure 13E:
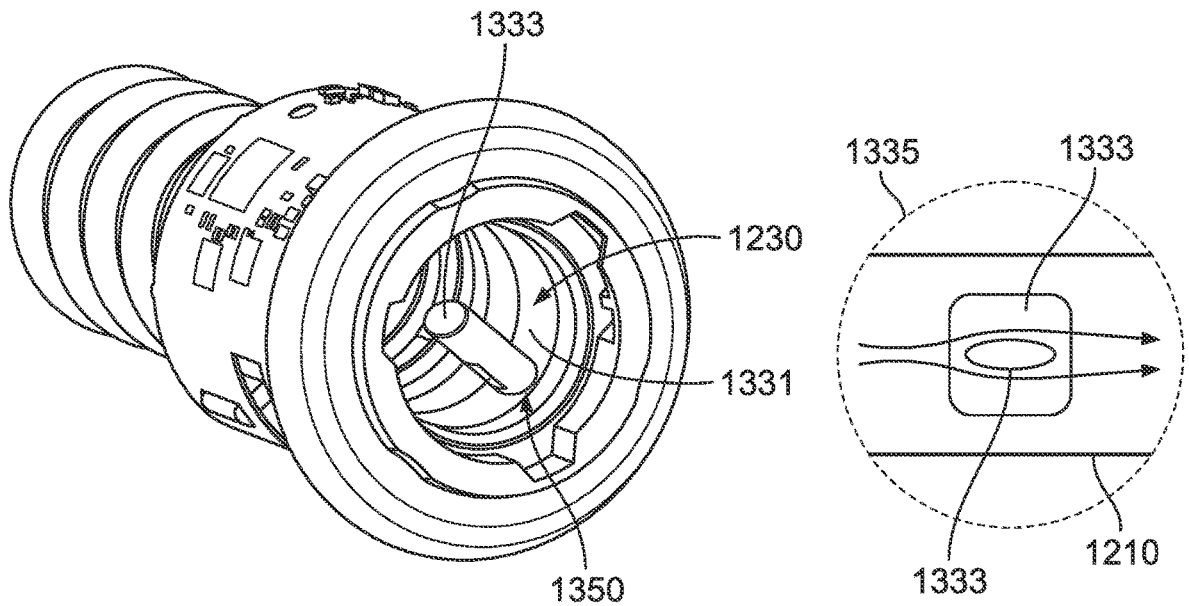

Such an insertion of the flexible extension strip sensor may be considered in relation to FIGS. 13D and 13E. FIG. 13D shows the sensor case 1230 inserted over a sensor(s) of the extension strip 1009 of the circuit board 1205 so as to cover one or more sensor(s) of the printed circuit board. The sensor(s) and case may then be inserted through the sensor aperture in the delivery conduit connector end so that they are positioned within the conduit and so that the sensor is capable of measuring one or more characteristics of the breathable gas, such as its temperature or humidity, etc. In FIG. 13E, the covered sensor and its case 1230 can be seen protruding through a sensor aperture 1350 in the delivery conduit connector end 1210. As illustrated, the sensor case 1230 includes a base portion 1331 that corresponds to the sensor aperture and the contour of the inside gas passage surface of the connector end so as to smoothly seal the sensor aperture with the contour of the surface of the gas passage when inserted into the aperture. The base also permits proper orientation of the sensor case within the connector end. In this regard, the sensor case also extends the sensor into the gas passage at a sensor end 1333 of the sensor case. In this version, the sensor end 1333 of the sensor case has an aerodynamic profile to minimize gas flow resistance with the flow of air though the gas passage of the delivery conduit connector end as it travels around the sensor end. For example, the sensor end 1333 of the case may have an oval profile as seen in a cross sectional plan view 1335 (also shown in FIG. 13E) of the cuff and the sensor case within the airflow path/passage of cuff.

Figure 13F:
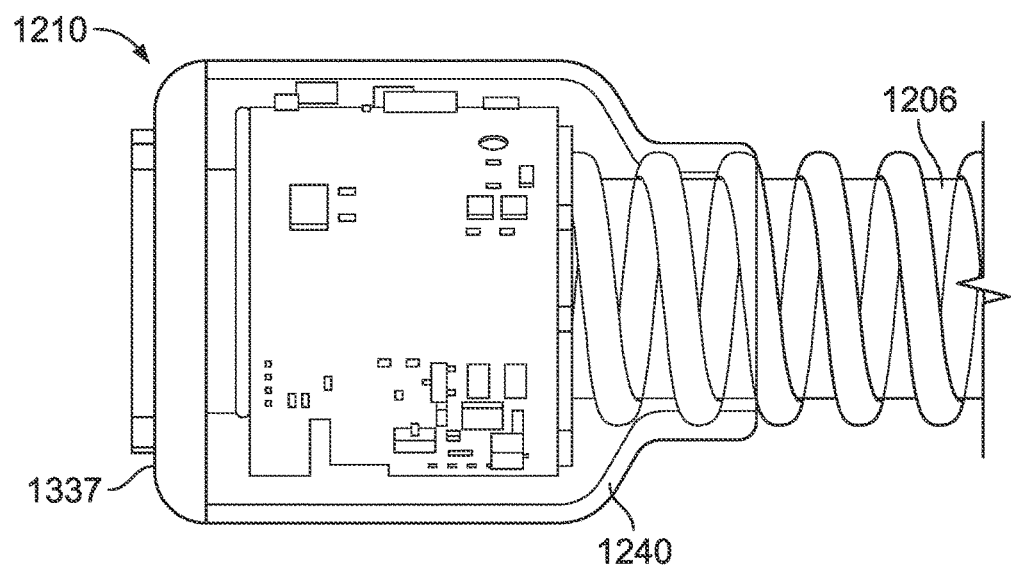

FIG. 13F illustrates the application of the outer casing 1240. Such a casing or sheath component may be slideably engaged over the hollow tubing portion 1206 until coming into contact with the seat end 1337 of delivery conduit connector end 1210. The casing 1240 may then be affixed to the delivery conduit connector end 1210, for instance using an ultra-sonic welder or other affixing method. Thus, the casing may seal therein the electrical components of the delivery conduit connector end and seal the delivery conduit end against air leaks from the passage within the cuff.

In one example, the delivery conduit shown in FIG. 13F may comprise a wireless transceiver as described elsewhere in the present specification, and configured to communicate with a patient interface. The wireless transceiver may be an NFC reader, and may be configured to communicate with an NFC tag located on the patient interface, such as when the patient interface is connected to the delivery conduit or is put in proximity thereto. The patient interface may comprise a connector configured to be inserted into the cuff of the delivery conduit, wherein the connector comprises the NFC tag. The delivery conduit may in use generate a signal indicating some or all of the information obtained from the NFC tag, such as a type or age of the patient interface, to the controller 120.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

The invention claimed is:

1. A respiratory apparatus comprising:
   a respiratory therapy device to generate a flow of breathable gas;
   a delivery conduit to conduct the generated flow of breathable gas from the respiratory therapy device to a patient interface;
   a first controller located at the respiratory therapy device;
   a second controller located at or adjacent to a patient-end of the delivery conduit; and
   a set of wires along the delivery conduit connecting the first controller and the second controller, the set of wires comprising three wires for both heating of the delivery conduit and for data communication between the first controller and the second controller,
   wherein one or both of the first controller and second controller is configured to interleave communication operations and heating operations in alternating fashion through the set of wires.

2. The apparatus of claim 1, wherein the set of wires comprises a first wire, a second wire, and a ground wire, wherein the first wire and ground wire provide for data communication between the first controller and the second controller, and wherein the second wire and said ground wire provide heat for the delivery conduit using power from a power supply of the respiratory therapy device.

3. The apparatus of claim 1, further comprising a first switch located at the respiratory therapy device and controlled by the first controller, and a second switch located at the delivery conduit and controlled by the second controller.

4. The apparatus of claim 3, wherein closing each of the first switch and the second switch controls the heating operations.

5. The apparatus of claim 2, wherein closing the first switch and opening the second switch permits control of the communication operations.

6. The apparatus of claim 4, wherein the communication operation comprises a transmission of a measurement from one or more sensors in the delivery conduit.

7. The apparatus of claim 6, wherein the one or more sensors are configured to measure at least one of air flow, pressure, temperature, and relative humidity in the delivery conduit.

8. The apparatus of claim 5, wherein the communication operation comprises a transmission of an identification of an accessory coupled to the delivery conduit.

9. The apparatus of claim 1, further comprising a cuff and sheath attached to the patient end of the delivery conduit, wherein the second controller is disposed on the cuff and covered by the sheath.

10. A control method for a respiratory apparatus, the respiratory apparatus including a respiratory therapy device to generate a flow of breathable gas, a delivery conduit to conduct the generated flow of breathable gas from the respiratory therapy device to a patient interface, and a set of wires to couple a first controller with a second controller, the set of wires extending along the delivery conduit and separating the first controller and the second controller, the control method comprising:

receiving data through the set of wires at the first controller in a communications operation;

transmitting the data through the set of wires from the second controller in said communications operation;

heating the set of wires with one or both of the first controller and second controller in a heating operation to heat a flow of breathable gas through the delivery conduit; and interleaving the heating operation and the communications operation.

11. The control method of claim 10, wherein the data of the communications operation indicates one or more of flow, pressure, temperature, and relative humidity of the breathable gas flowing through the delivery conduit.

12. The control method of claim 10, wherein the heating operation is controlled by a pulse width modulation signal.

13. The control method of claim 11, wherein the heating operation is controlled by a pulse width modulation signal.

* * * * *